(12) United States Patent
Watson et al.

(10) Patent No.: US 11,328,022 B2
(45) Date of Patent: May 10, 2022

(54) SYSTEM FOR DOCUMENT RANKING BY PHRASE IMPORTANCE

(71) Applicant: S&P Global Inc., New York, NY (US)

(72) Inventors: William Watson, New York, NY (US); Lawrence Yong, Newport, NJ (US); Mingyang Di, Newport, NJ (US); Armineh Nourbakhsh, Brooklyn, NY (US)

(73) Assignee: S&P Global Inc., New York, NY (US)

(*) Notice: Subject to any disclaimer, the term of this patent is extended or adjusted under 35 U.S.C. 154(b) by 123 days.

(21) Appl. No.: 16/821,311

(22) Filed: Mar. 17, 2020

(65) Prior Publication Data

US 2021/0294859 A1  Sep. 23, 2021

(51) Int. Cl.
*G06F 17/00* (2019.01)
*G06F 16/903* (2019.01)
*G06F 16/9038* (2019.01)
*G06N 20/00* (2019.01)

(52) U.S. Cl.
CPC .... *G06F 16/90344* (2019.01); *G06F 16/9038* (2019.01); *G06N 20/00* (2019.01)

(58) Field of Classification Search
CPC .......... G06F 16/90344; G06F 16/9038; G06N 20/00; G06N 3/126; G06N 5/003; G06N 5/025; G06N 5/045; G06N 7/005
See application file for complete search history.

(56) References Cited

U.S. PATENT DOCUMENTS

| | | | | |
|---|---|---|---|---|
| 6,101,491 A * | 8/2000 | Woods | ..................... | G06F 16/30 707/696 |
| 8,060,455 B2 * | 11/2011 | Liu | ........................ | G06N 20/00 706/12 |
| 10,810,214 B2 * | 10/2020 | Huang | ................. | G06F 16/9535 |
| 2011/0131205 A1 * | 6/2011 | Iyer | ...................... | G06F 16/3334 707/728 |
| 2015/0074033 A1 * | 3/2015 | Shah | ........................ | G06N 5/02 706/46 |
| 2018/0101617 A1 * | 4/2018 | Govindarajan | ..... | G06F 16/9535 |

OTHER PUBLICATIONS

Lorena Leal Bando, Falk Scholer, and Andrew Turpin. Constructing query-biased summaries: a comparison of human and system generated snippets. In Proceedings of the third symposium on Information interaction in context, Association for Computing Machinery, 195-204, Aug. 2010.*

* cited by examiner

*Primary Examiner* — Greta L Robinson
(74) *Attorney, Agent, or Firm* — Yee & Associates, P.C.

(57) ABSTRACT

A method, apparatus, system, and computer program product for searching for documents. A query comprising search terms is received. A search is performed on a collection of documents for each search term in the search terms. Search results are received for the search terms. Each search result includes documents from the collection of documents containing a search term in the search terms and scores associated with the documents. Aggregate scores for the search terms in the search results are associated with each document in the documents returned to form combined results in which a combined result in the combined results comprises the document and an aggregate score associated with the document. The documents in the combined results are ranked based on the aggregate scores to form a ranked order for the documents. The combined results with the aggregate scores in the ranked order are displayed on a display system.

34 Claims, 14 Drawing Sheets

Search Terms — 604

( RMBS ⊗ ) ( Loss Severity ⊗ ) ( Foreclosure Frequency ⊗ ) ( Archetypal Pool ⊗ )

Showing top 10 of 92 results

ARCHIVE | Criteria | Structured Finance | RMBS: Methodology And Assumptions: Assessing Pools Of Residential Loans in France And Belgium
http://www.cap.com/ABCDotNet/CreditResearch/CDResearch.aspx?8&From=SNP_CRS
Nov 18, 2016 - RMBS,Loss Severity,Foreclosure Frequency,Archetypal Pool ARCHIVE | Criteria | Structured Finance | RMBS: Methodology And Assumptions: Assessing Pools Of Residential Loans
in Austria, Denmark, Germany, And Sweden
http://www.cap.com/ABCDotNet/CreditResearch/CDResearch.aspx?8&From=SNP_CRS
Jun 23, 2017 - RMBS,Loss Severity,Foreclosure Frequency,Archetypal Pool Criteria | Structured Finance | General: Methodology And Assumptions: Assessing Pools Of European Residential Loans
http://www.cap.com/ABCDotNet/CreditResearch/CDResearch.aspx?8&From=SNP_CRS
Aug 4, 2017 - RMBS,Loss Severity,Foreclosure Frequency,Archetypal Pool ARCHIVE | Criteria | Structured Finance | General: Methodology And Assumptions: Assessing Pools Of European Residential Loans
http://www.cap.com/ABCDotNet/CreditResearch/CDResearch.aspx?8&From=SNP_CRS
Dec 23, 2016 - RMBS,Loss Severity,Foreclosure Frequency,Archetypal Pool Criteria | Structured Finance | RMBS: Global Methodology And Assumptions: Assessing Pools Of Residential Loans
http://www.cap.com/ABCDotNet/CreditResearch/CDResearch.aspx?8&From=SNP_CRS
Jan 25, 2019 - RMBS,Loss Severity,Foreclosure Frequency,Archetypal Pool Criteria | Structured Finance | RMBS: Global Methodology And Assumptions: Assessing Pools Of Residential Loans
http://www.cap.com/ABCDotNet/CreditResearch/CDResearch.aspx?8&From=SNP_CRS
Jan 25, 2019 - RMBS,Loss Severity,Foreclosure Frequency,Archetypal Pool

FIG. 7

| title | date | rank 808 | RMBS 810 811 | Loss Severity 814 816 | Foreclosure Frequency 818 | Archetypal Pool 820 |
|---|---|---|---|---|---|---|
| ARCHIVE \| Criteria \| Structured Finance \| RMBS: Methodology And | Nov 18, 2016 | 26.75 | 3.16 | 4.89 | 7.17 | 11.54 |
| ARCHIVE \| Criteria \| Structured Finance \| RMBS: Methodology And | Jun 23, 2017 | 26.65 | 3.09 | 4.84 | 7.42 | 11.30 |
| Criteria \| Structured Finance \| General: Methodology And Assumpt | Aug 4, 2017 | 26.60 | 3.00 | 4.80 | 7.40 | 11.40 |
| ARCHIVE \| Criteria \| Structured Finance \| General: Methodology A | Dec 23, 2016 | 26.56 | 3.10 | 4.78 | 7.37 | 11.31 |
| Criteria \| Structured Finance \| RMBS: Global Methodology And Ass | Jan 25, 2019 | 25.75 | 3.08 | 4.75 | 7.24 | 10.68 |
| Criteria \| Structured Finance \| RMBS: Global Methodology And Ass | Jan 25, 2019 | 25.72 | 2.96 | 4.77 | 7.25 | 10.74 |
| Guidance \| Criteria \| Structured Finance \| RMBS: Global Methodol | Jan 25, 2019 | 24.23 | 3.02 | 3.81 | 7.18 | 10.23 |
| Guidance \| Criteria \| Structured Finance \| RMBS: Global Methodol | Jan 25, 2019 | 23.95 | 2.97 | 3.95 | 7.16 | 9.86 |
| Criteria \| Structured Finance \| RMBS: Methodology And Assumption | Feb 25, 2018 | 23.94 | 3.16 | 4.85 | 7.35 | 8.59 |
| Guidance \| Criteria \| Structured Finance \| General: Criteria For | Jan 19, 2018 | 15.46 | 3.05 | 2.55 | 3.84 | 6.02 |
| Criteria \| Structured Finance \| RMBS: Australian RMBS Rating Met | Aug 30, 2011 | 15.37 | 3.17 | 4.74 | 7.47 | 0.00 |
| Criteria \| Structured Finance \| RMBS: Methodology And Assumption | Dec 19, 2014 | 15.24 | 3.26 | 4.88 | 7.10 | 0.00 |

FIG. 8

Rows: 40

Cell Value (Click on a cell)

🔍 SEARCH TOOL

⬇ Export — 806

800 / 802 / 804

| title | date | rank | RMBS | Loss Severity | Foreclosure Frequency | Archetypal Pool |
|---|---|---|---|---|---|---|
| ARCHIVE \| Criteria \| Structured Finance \| RMBS: Dutch RMBS Metho | Dec 27, 2015 | 14.38 | 3.32 | 4.55 | 6.51 | 0.00 |
| Guidance \| Criteria \| Structured Finance \| RMBS: Methodology And | Jan 16, 2019 | 10.97 | 3.30 | 0.00 | 0.00 | 7.67 |
| Guidance \| Criteria \| Structured Finance \| RMBS: Methodology And | Jan 16, 2019 | 10.97 | 3.30 | 0.00 | 0.00 | 7.67 |
| Criteria \| Structured Finance \| RMBS: Methodology And Assumption | Jun 5, 2010 | 5.40 | 3.28 | 2.12 | 0.00 | 0.00 |
| Criteria \| Structured Finance \| RMBS: Methodology And Assumption | Mar 4, 2016 | 8.06 | 3.28 | 4.78 | 0.00 | 0.00 |
| Criteria \| Structured Finance \| RMBS: New Zealand RMBS Rating Me | Sep 17, 2011 | 7.90 | 3.27 | 0.00 | 4.63 | 0.00 |
| Criteria \| Structured Finance \| RMBS: Methodology And Assumption | Dec 19, 2014 | 15.24 | 3.26 | 4.88 | 7.10 | 0.00 |
| General Criteria: U.S. Government Support in Structured Finance | Dec 9, 2014 | 6.32 | 3.20 | 3.12 | 0.00 | 0.00 |
| Criteria \| Structured Finance \| RMBS: Assumptions Supplement For | Feb 25, 2018 | 14.50 | 3.19 | 4.25 | 7.06 | 0.00 |
| Criteria \| Structured Finance \| RMBS: Methodology And Assumption | Mar 15, 2013 | 7.57 | 3.17 | 4.41 | 0.00 | 0.00 |
| Criteria \| Structured Finance \| RMBS: Rating Methodology And Ass | Jan 31, 2008 | 14.30 | 3.17 | 4.18 | 6.95 | 0.00 |
| Criteria \| Structured Finance \| RMBS: Australian RMBS Rating Met | Aug 30, 2011 | 15.37 | 3.17 | 4.74 | 7.47 | 0.00 |

FIG. 9

SYSTEM FOR DOCUMENT RANKING BY PHRASE IMPORTANCE

BACKGROUND INFORMATION

1. Field

The present disclosure relates generally to an improved computer system and, in particular, to a method, apparatus, system, and computer program product for ranking documents in response to a search input containing multiple terms.

2. Background

A search engine is a software system that operates to search a collection of documents for information that is specified in a search query. Commonly available search engines are web search engines that are used to search information on the Internet. The search results are typically presented on a web page generated by the search engine. Information, in the search results can include links to webpages, images, videos documents, and other types of files.

Search engines, however, return search results on keywords in the search query. The search results, however, can be so numerous that it can be impractical for a user to review the search results to identify documents or other information relevant to what that the user is looking for in performing the search.

Therefore, it would be desirable to have a method and apparatus that take into account at least some of the issues discussed above, as well as other possible issues. For example, it would be desirable to have a method and apparatus that overcome a technical problem with increasing the usefulness of search results.

SUMMARY

An embodiment of the present disclosure provides a document search system comprising a computer system and a search manager in the computer system. The search manager is configured to receive a query comprising search terms. The search manager is configured to perform a search on a collection of documents for each search term in the search terms. The search manager is configured to receive search results for the search terms, wherein each search result includes documents from the collection of documents containing a search term in the search terms and scores associated with the documents, wherein a score in the scores indicates an importance of the search term to a document in the collection of documents searched using the search term. The search manager is configured to associate aggregate scores for the search terms in the search results with the documents returned in the searches to form combined results in which a combined result in the combined results comprises the document in the documents and an aggregate score associated with the document. The search manager is configured to rank the documents in the combined results in the search based on the aggregate scores to form a ranked order for the documents. The search manager is configured to display, on a display system, the combined results with the aggregate scores in the ranked order.

Another embodiment of the present disclosure provides a method for searching for documents. A query comprising search terms is received by the computer system. A search is performed by the computer system on a collection of documents for each search term in the search terms. Search results are received by the computer system for the search terms. Each search result includes documents from the collection of documents containing a search term in the search terms and scores associated with the documents. A score in the scores indicates an importance of the search term to a document in the collection of documents searched using the search term. Aggregate scores for the search terms in the search results are associated by the computer system with each document in the documents returned in the searches to form combined results in which a combined result in the combined results comprises the document and an aggregate score associated with the document. The documents in the combined results in the search are ranked by the computer system based on the aggregate scores to form a ranked order for the documents. The combined results with the aggregate scores in the ranked order are displayed on a display system by the computer system.

Still another embodiment of the present disclosure provides a computer program product for searching for documents. The computer program product comprises a computer-readable storage media and first program code, second program code, third program code, fourth program code, fifth program code, and sixth program code stored on the computer-readable storage media. The first program code is executable by a computer system to cause the computer system to receive a query comprising search terms. The second program code is executable by the computer system to cause the computer system to perform a search on a collection of documents for each search term in the search terms. The program code executable by the computer system to cause the computer system to receive search results for the search terms. Each search result includes documents from the collection of documents containing the search term in the search terms and scores associated with the documents. A score in the scores indicates an importance of the search term to a document in the collection of documents searched using the search term. The fourth program code executable by the computer system to cause the computer system to associate aggregate scores for the search terms in the search results with the documents returned in the searches to form combined results in which a combined result in the combined results comprises the document in the documents and an aggregate score associated with the document. The fifth program code is executable by the computer system to cause the computer system to rank the documents in the combined results in the search based on the aggregate scores to form a ranked order for the documents. The sixth program code is executable by the computer system to cause the computer system to display, on a display system, the combined results with the aggregate scores in the ranked order.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 7 is an illustration of search results in accordance with an illustrative embodiment;

FIG. 8 is an illustration of search results including a heat map in accordance with an illustrative embodiment;

FIG. 9 is another illustration of search results including a heat map in accordance with an illustrative embodiment;

DETAILED DESCRIPTION

Figure 1:
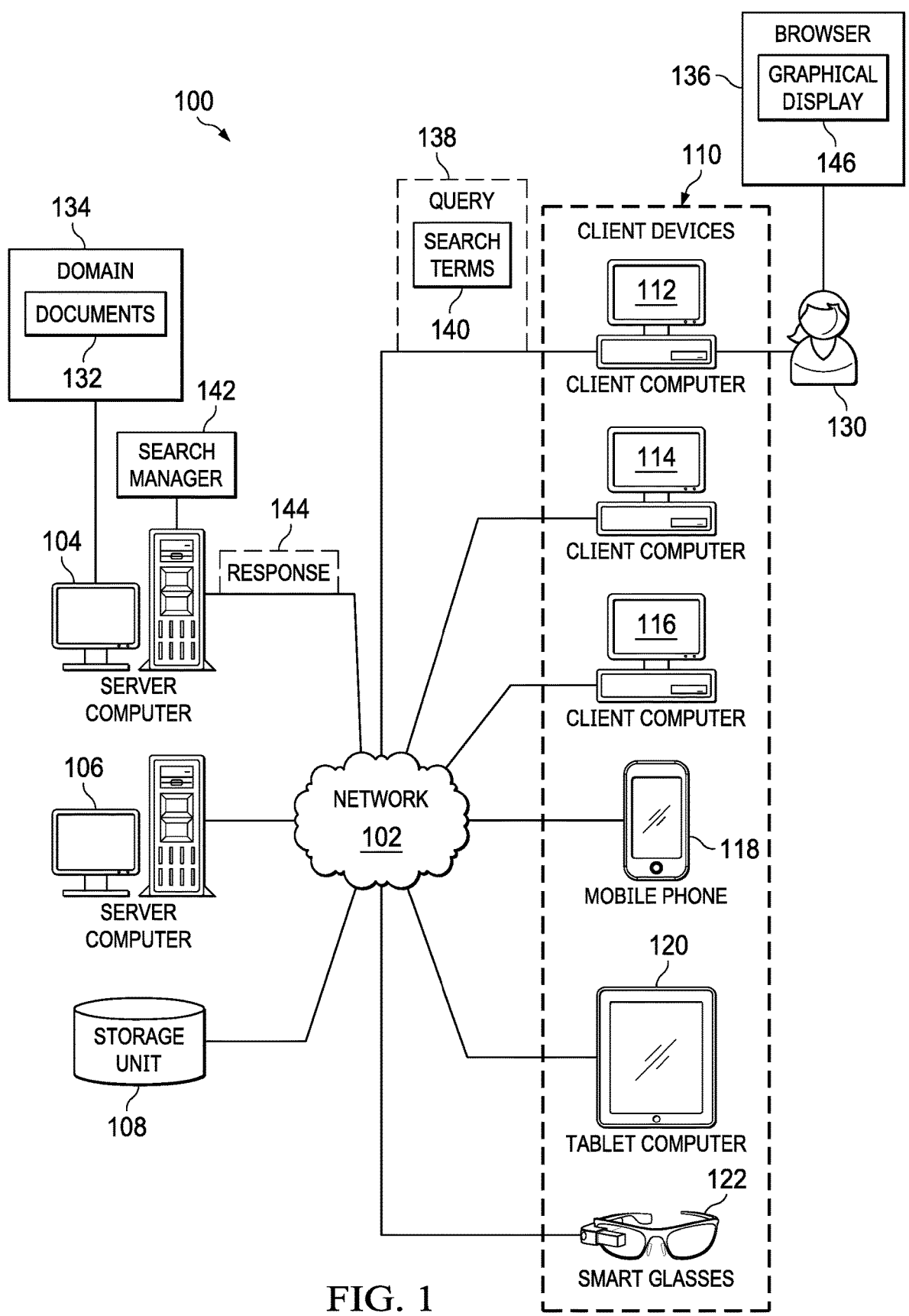
FIG. 1 is a pictorial representation of a network of data processing systems in which illustrative embodiments may be implemented.

The illustrative embodiments recognize and take into account one or more different considerations. For example, the illustrative embodiments recognize and take into account that it can be desirable to search for documents in a particular domain such as criteria documents containing ratings of organizations using criteria for analyzing the organizations. The illustrative embodiments recognize and take into account that searches can be performed using search terms.

As used herein, a "search term" is a word, a combination of words, or a phrase. In the illustrative example, the search term can be used when searching for information from a collection of information. The information can be, for example, at least one of a document, a webpage, a video, an audio file, an image, a spreadsheet, or some other type of information.

Further, the phrase "at least one of," when used with a list of items, means different combinations of one or more of the listed items can be used, and only one of each item in the list may be needed. In other words, "at least one of" means any combination of items and number of items may be used from the list, but not all of the items in the list are required. The item can be a particular object, a thing, or a category.

For example, without limitation, "at least one of item A, item B, or item C" may include item A, item A and item B, or item B. This example also may include item A, item B, and item C or item B and item C. Of course, any combinations of these items can be present. In some illustrative examples, "at least one of" can be, for example, without limitation, two of item A; one of item B; and ten of item C; four of item B and seven of item C; or other suitable combinations.

However, the illustrative embodiments recognize and take into account that search results returned based on these search terms can be too numerous to practically review. The illustrative embodiments recognize and take into account that search engines rank the search results but do not provide a user with an idea of the search results' relevancy to particular search terms.

Further, the illustrative embodiments recognize and take into account that current search engines do not calculate relevance based on the entire document. The illustrative embodiments recognize and take into account that current search engines use a title and may use a single page in the document rather than analyzing the entire document. Further, the illustrative embodiments recognize and take into account that current search engines do not focus on a specific domain such as financial documents, criterion documents for rating organization, or technical and scientific documents.

Thus, it would be desirable to have a method, apparatus, system, and computer program product that search for documents using search terms in a manner that provides search results that indicate a level of relevancy to the search performed.

In one illustrative example, a method for searching for documents is provided. A query comprising search terms is received by a computer system. A search is performed by the computer system on a collection of documents for each search term in the search terms. Search results are received by the computer system for the search terms. Each search result includes documents from the collection of documents containing a search term in the search terms and scores associated with the documents. A score in the scores indicates an importance of the search term to a document in the collection of documents searched using the search term. Aggregate scores for the search terms in the search results are associated by the computer system with each document in the documents returned in the searches to form combined results in which a combined result in the combined results comprises the document and an aggregate score associated with the document. The documents in the combined results in the search are ranked by the computer system based on the aggregate scores to form a ranked order for the documents. The combined results with the aggregate scores in the ranked order are displayed on a display system by the computer system.

With reference now to the figures and, in particular, with reference to FIG. 1, a pictorial representation of a network of data processing systems is depicted in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server computer 104 and server computer 106 connect to network 102 along with storage unit 108. In addition, client devices 110 connect to network 102. As depicted, client devices 110 include client computer 112, client computer 114, and client computer 116. Client devices 110 can be, for example, computers, workstations, or network computers. In the depicted example, server computer 104 provides information, such as boot files, operating system images, and applications to client devices 110. Further, client devices 110 can also include other types of client devices such as mobile phone 118, tablet computer 120, and smart glasses 122. In this illustrative example, server computer 104, server computer 106, storage unit 108, and client devices 110 are network devices that connect to network 102 in which network 102 is the communications media for these network devices. Some or all of client devices 110 may form an Internet-of-things (IoT) in which these physical devices can connect to network 102 and exchange information with each other over network 102.

Client devices 110 are clients to server computer 104 in this example. Network data processing system 100 may include additional server computers, client computers, and other devices not shown. Client devices 110 connect to network 102 utilizing at least one of wired, optical fiber, or wireless connections.

Program code located in network data processing system 100 can be stored on a computer-recordable storage medium and downloaded to a data processing system or other device for use. For example, program code can be stored on a computer-recordable storage medium on server computer 104 and downloaded to client devices 110 over network 102 for use on client devices 110.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers consisting of thousands of commercial, governmental, educational, and other computer systems that route data and messages. Of course, network data processing system 100 also may be implemented using a number of different types of networks. For example, network 102 can be comprised of at least one of the Internet, an intranet, a local area network (LAN), a metropolitan area network (MAN), or a wide area network (WAN). FIG. 1 is intended as an example, and not as an architectural limitation for the different illustrative embodiments.

As used herein, a "number of," when used with reference to items, means one or more items. For example, a "number of different types of networks" is one or more different types of networks.

In this illustrative example, user 130 can perform a search for documents 132 in domain 134 in server computer 104. Documents 132 in domain 134 can take a number of different forms. In this example, documents 132 in domain 134 can be selected from at least one of criteria documents for financially evaluating organizations, research documents, technical papers, manufacturing specifications, or other suitable types of documents. Domain 134 may include a single type of document or may include many types of documents.

The search can be performed by user 130 interacting with browser 136 at client computer 112. In this illustrative example, browser 136 is a software application for accessing information on network data processing system 100. For example, browser 136 can retrieve content from a server computer such as server computer 104 and display the information on client computer 112. In this illustrative example, browser 136 can be, for example, a web browser.

Through this interaction, user 130 can generate query 138 containing search terms 140. Query 138 is sent to search manager 142 running on server computer 104. Search manager 142 performs a search on domain 134 with each of the search terms in search terms 140. Another search is performed individually for each search term.

A result is received for each of the searches in which each result contains an identification of a number of documents 132 and scores for the number of documents 132. In this illustrative example, the collection of documents 132 can be stored in a database that implements currently-used processes for generating scores. A score in the scores indicates an importance of a term to a document in documents 132 in domain 134.

In this illustrative example, search manager 142 aggregates the scores from the different searches to form aggregate scores for the search terms in the search results for each document in the documents returned in the searches. These aggregate scores are associated with the documents such that each document has an aggregate score based on the search term for which the document was returned.

The documents in the combined results are ranked by search manager 142 based on the aggregate scores to form a ranked order in the depicted example. The process then returns the combined results in the ranked order in response 144 to browser 136.

In this illustrative example, browser 136 displays the combined results in the ranked order on a display system in client computer 112 to user 130. In the illustrative example, the display of the combined results includes displaying an identification of the documents and the relevance of the search terms for each of the documents in a combined result.

The display of the combined results in the ranked order on the display system can be graphical display 146 in a window for browser 136. Graphical display 146 is designed to provide user 130 with an ability to more quickly determine the relevance of individual search terms using graphical elements and indicators that are organized or configured to aid in determining the relevance of individual search terms as compared to current techniques which do not display scores for search terms with search results. Graphical display 146 provides an enhanced manner for presenting the combined results as compared to other illustrative examples in which the combined results are displayed without a graphical indication of the relevance of individual search terms in other illustrative examples.

The illustration of network data processing system 100 is only an illustrative example of one implementation for an illustrative embodiment. For example, documents in addition to or in place of documents 132 in other domains in addition to or in place of domain 134 can be located in server computer 104. In other illustrative examples, these documents in the domains can be located on another server such as server computer 106.

In still another illustrative example, documents 132 in domain 134 can be distributed in different locations in addition to or in place of server computer 104. For example, documents 132 can be located in at least one of server computer 106, storage unit 108, or client computer 114. In another illustrative example, user 130 can perform a search from other client devices such as mobile phone 118, tablet computer 120, or smart glasses 122.

Figure 2:
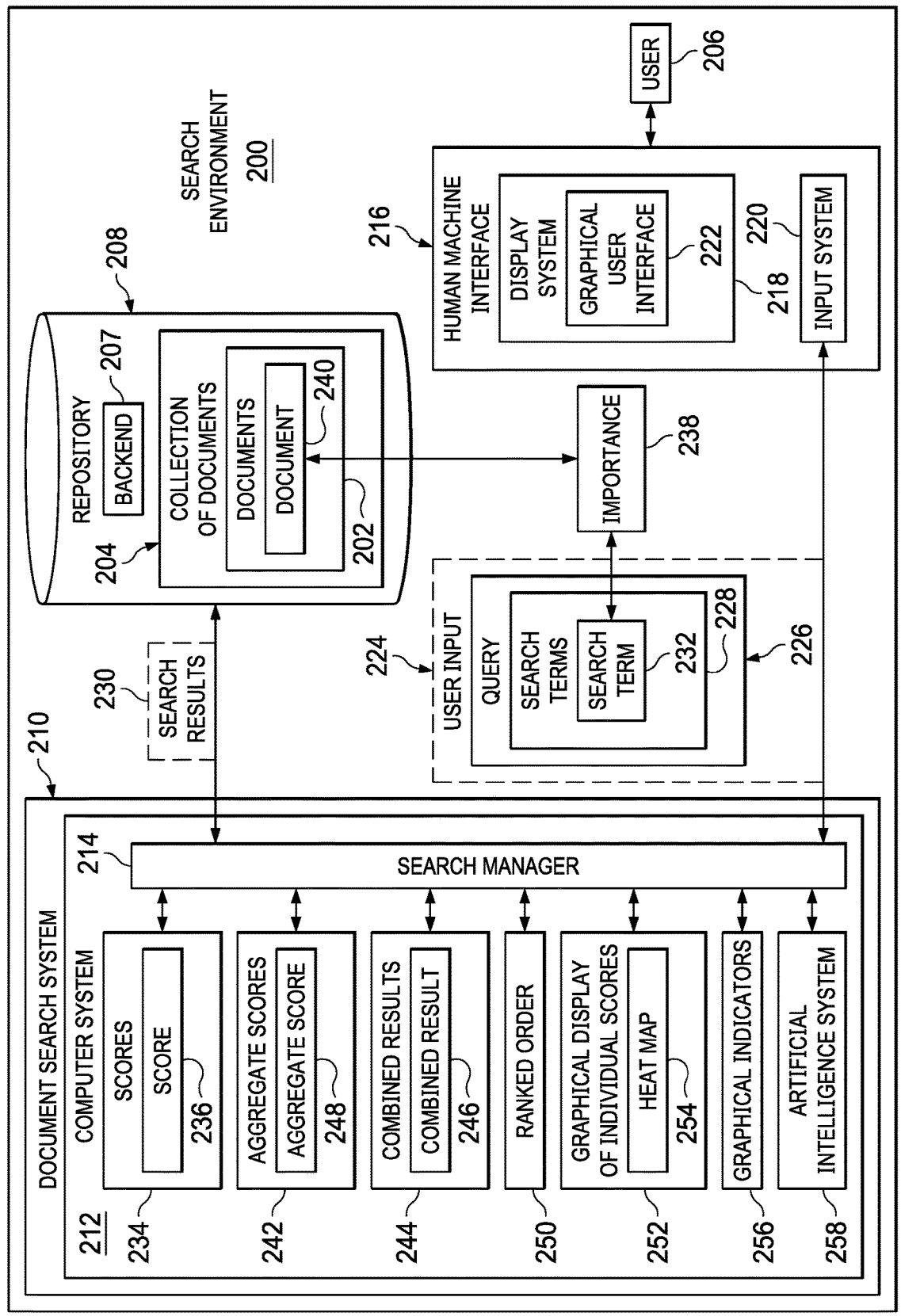
FIG. 2 is a block diagram of a search environment in accordance with an illustrative embodiment.

With reference now to FIG. 2, a block diagram of a search environment is depicted in accordance with an illustrative embodiment. In this illustrative example, search environment 200 includes components that can be implemented in hardware such as the hardware shown in network data processing system 100 in FIG. 1.

In this illustrative example, documents 202 in collection of documents 204 can be searched by user 206 to identify documents 204 that may be desired for various purposes. Documents 204 can take a number of different forms. For example, documents 204 can be selected from at least one of a criteria document, a technical article, a journal article, a patent, a manufacturing specification, an electronic book, or other suitable types of documents.

In this illustrative example, documents 202 in collection of documents 204 can be located in repository 208. Repository 208 is a hardware system and can include one or more storage devices. For example, repository 208 can be implemented using at least one of a hard disk, a flash drive, a solid-state disk drive, a storage area network, a tape drive, a disk array, or other suitable types of storage devices.

In this illustrative example, repository 208 can also include backend 207. In this illustrative example, backend 207 is a search engine that can be used to search a database containing collection of documents 204. Backend 207 can be, for example, an Elasticsearch search engine. The search engine is available from Elasticsearch B.V. Elasticsearch is a registered trademark of Elasticsearch B.V.

In this illustrative example, user 206 can perform a search of documents 202 in collection of documents 204 using document search system 210. The search is performed through a mechanism such as human machine interface 216. As depicted, human machine interface 216 comprises display system 218 and input system 220.

Display system 218 in human machine interface 216 is a physical hardware system and includes one or more display devices on which graphical user interface 222 can be displayed. The display devices can include at least one of a light emitting diode (LED) display, a liquid crystal display (LCD), an organic light emitting diode (OLED) display, a computer monitor, a projector, a flat panel display, a heads-up display (HUD), or some other suitable device that can output information for the visual presentation of information.

In this illustrative example, user 206 is a person that can interact with graphical user interface 222 through user input 224 generated by input system 220 in human machine interface 216. Input system 220 is a physical hardware system and can be selected from at least one of a mouse, a keyboard, a trackball, a touchscreen, a stylus, a motion-sensing input device, a gesture detection device, a cyber glove, or some other suitable type of input device.

As depicted, document search system 210 comprises computer system 212 and search manager 214. Search manager 214 is located in computer system 212.

Search manager 214 can be implemented in software, hardware, firmware, or a combination thereof. When software is used, the operations performed by search manager 214 can be implemented in program code configured to run on hardware, such as a processor unit. When firmware is used, the operations performed by search manager 214 can be implemented in program code and data and stored in persistent memory to run on a processor unit. When hardware is employed, the hardware may include circuits that operate to perform the operations in search manager 214.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device can be configured to perform the number of operations. The device can be reconfigured at a later time or can be permanently configured to perform the number of operations. Programmable logic devices include, for example, a programmable logic array, a programmable array logic, a field programmable logic array, a field programmable gate array, and other suitable hardware devices. Additionally, the processes can be implemented in organic components integrated with inorganic components and can be comprised entirely of organic components excluding a human being. For example, the processes can be implemented as circuits in organic semiconductors.

Computer system 212 is a physical hardware system and includes one or more data processing systems. When more than one data processing system is present in computer system 212, those data processing systems are in communication with each other using a communications medium. The communications medium may be a network. The data processing systems may be selected from at least one of a computer, a server computer, a tablet, or some other suitable data processing system.

In this illustrative example, search manager 214 in computer system 212 is configured to perform a number of different operations or steps. For example, search manager 214 can receive query 226 comprising search terms 228. In this illustrative example, a search term in search terms 228 is a word or a phrase. Query 226 can be received in user input 224.

Search manager 214 can perform a search on collection of documents 204 for each search term in search terms 228. In this example, search terms 228 can be searched individually. In other words, search manager 214 initiates a search for each search term. Further, the search performed using search terms 228 on collection of documents 204 can be performed using a fuzzy searching process. In other words, the search does not have to be for an exact match to search terms 228.

As depicted, search manager 214 receives search results 230 for search terms 228. Each search result includes documents 202 from collection of documents 204 containing search term 232 in search terms 228 and scores 234 associated with documents 202. In this illustrative example, search results 230 can be received from backend 207. Backend 207 also is configured to provide scores 234. For example, an Elasticsearch search engine currently provides these scores in search results 230. Another example of a search engine that can be used in backend 207 is Apache Lucene, which is an open source search engine.

In the illustrative example, score 236 in scores 234 indicates importance 238 of search term 232 to document 240 in collection of documents 204 searched using search term 232. In this example, scores 234 can be term frequency-inverse document frequency (tf-idf) scores. Term frequency-inverse document frequency (tf-idf) scores are numerical statistics and reflect how important a word is to a document in a collection of documents. The value of the score increases proportionally to the number of times a search term appears in a document is offset by the number of documents in the collection of documents that contain the search term. Other techniques can be used for determining the importance of words in documents.

Scores 234 can be commonality scores. A commonality score for the search term is based on a number of times the search term is present in the document and the number of times the search term is present in all documents subject to the search.

An example of another mechanism that can be used to generate scores that indicate the importance of a word in a document in relationship to other documents in collection of documents 204 is a bag of words model.

In this illustrative example, search manager 214 can generate aggregate scores 242 for search terms 228. Search manager 214 can associate aggregate scores 242 for search terms 228 in search results 230 with documents 202 returned in the searches to form combined results 244 in which combined result 246 in combined results 244 comprises document 240 in documents 202 and aggregate score 248 associated with document 240.

Additionally, search manager 214 can rank documents 202 in combined results 244 in the search based on aggregate scores 242 to form ranked order 250 for documents 202. Search manager 214 can display combined results 244 with aggregate scores 242 in ranked order 250 on display system 218.

In displaying combined results 244, search manager 214 can display a number of highest ranked combined results in combined results 244 with aggregate scores 242 for the number of highest ranked combined results in ranked order 250. For example, the number of highest ranked combined results can be the top 20, top 10, or some other number of ranked results having the highest scores. In other illustrative examples, every combined result in combined results 244 can be displayed.

In one illustrative example, search manager 214 displays combined results 244 in ranked order 250 with aggregate scores 242 and graphical display of individual scores 252 for search terms 228 associated with document 240 in each combined result in combined results 244. This display is made in graphical user interface 222 and display system 218. In one illustrative example, graphical display of individual scores 252 comprises heat map 254. In this illustrative example, scores 234 are the individual scores in graphical display of individual scores 252.

In an illustrative example, in displaying combined results 244 in ranked order 250 with aggregate scores 242 and a graphical display of individual scores 252 for search terms 228 associated with document 240 in each combined result in combined results 244, search manager 214 can identify score 236 for each search term contributing to aggregate score 248 in each combined result in combined results 244. Search manager 214 can select a graphical indicator for each score identified for each search term contributing to aggregate score 248 in each combined result in combined results 244 to form graphical indicators 256 that indicate how often search term 232 is present in document 240 relative to other search terms in document 240. Search manager 214 can display documents 202 in ranked order 250 based on combined results 244.

Additionally, search manager 214 can also display graphical indicators 256 for each of documents 202 in graphical association with documents 202. In this illustrative example, a graphical association with the document means that a graphical indicator is displayed in a manner that draws attention to the document. This graphical indicator can also provide information for the document for which attention is drawn. A graphical indicator can be displayed in graphical association by being displayed in a location proximate to the display of a document. Thus, the graphical indicator draws attention to the document that is graphically associated with the graphical indicator.

In this illustrative example, one or more of the different steps performed by search manager 214 can be performed using artificial intelligence system 258. An artificial intelligence system is a system that has intelligent behavior and can be based on the function of a human brain. In this illustrative example, artificial intelligence system 258 comprises at least one of an artificial neural network, a cognitive system, a Bayesian network, a fuzzy logic, an expert system, a natural language system, or some other suitable system. Machine learning is used to train the artificial intelligence system. Machine learning involves inputting data to the process and allowing the process to adjust and improve the function of the artificial intelligence system.

For example, the generation of at least one of scores 234, aggregate scores 242, combined results 244, ranked order 250, graphical display of individual scores 252, heat map 254, graphical indicators 256, or other results for information can be generated using artificial intelligence system 258.

Figure 3:
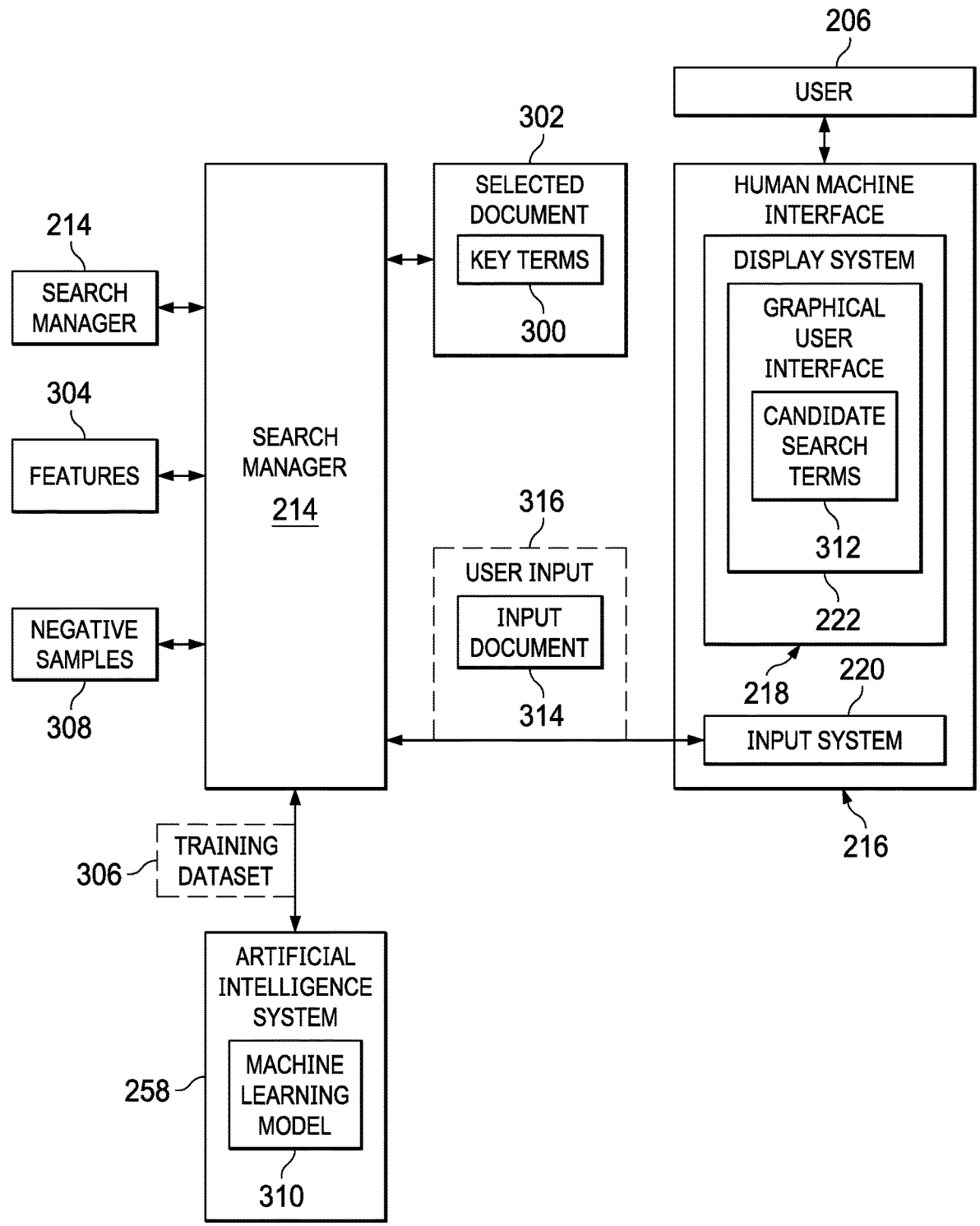
FIG. 3 is a dataflow for generating or suggesting search terms in accordance with an illustrative embodiment.

With reference next to FIG. 3, a dataflow for generating or suggesting search terms is depicted in accordance with an illustrative embodiment. In the illustrative examples, the same reference numeral may be used in more than one figure. This reuse of a reference numeral in different figures represents the same element in the different figures.

In this illustrative example, search manager 214 can be configured to generate search terms. For example, search manager 214 can identify a set of key terms 300 in selected document 302. In this illustrative example, a key term is a term that provides some representation of the whole document. A key term can be similar to the meaning or information provided in a summary or abstract of a document. For example, the key term for a document on foreclosures can be "foreclosure frequency".

The set of key terms 300 can be identified by search manager 214 in a number of different ways. For example, search manager 214 can use metadata for selected document 302. This metadata can be, for example, embedded or otherwise associated with selected document 302.

In one illustrative example, the metadata can be located in a table or validation report for selected document 302. For example, when selected document 302 is a criteria document providing ratings for organizations, the validation report can be a document that includes findings as to whether proposed criteria in selected document 302 are consistent with criteria documents. The metadata can be, for example, terms used in the validation report.

Selected document 302 can be a document not located in collection of documents 204. For example, selected document 302 can be a new criteria document that has not yet been added to collection of documents 204. In other illustrative examples, selected document 302 can be a document in collection of documents 204 in FIG. 2.

As depicted, search manager 214 can determine features 304 for key terms 300 in selected document 302. In this illustrative example, features 304 can be selected from at least one of a location of a key term, a context in which the key term is used with respect to other key terms, a term frequency—inverse document frequency (tf-idf) score for the term, how often the key term appears in other documents, how often the key term appears in other metadata for other documents, and other suitable information.

For example, the location of a key term can indicate the importance of a key term. For example, the use of the key term in at least one of a title, a heading, a subheading, or some other location in selected document 302 can be used to determine the importance of a key term for selected document 302.

In the illustrative example, at least one of a set of key terms 300 or features 304 and selected document 302 form training dataset 306. Additionally, search manager 214 can add negative samples 308 to training dataset 306 in which negative samples 308 include terms that are not key terms 300.

As depicted, search manager 214 can train machine learning model 310 in artificial intelligence system 258 using training dataset 306. In this illustrative example, machine learning model 310 is trained to determine an importance of candidate search terms 312 from input document 314 to recommend a set of candidate search terms 312.

Machine learning model 310 is a type of artificial intelligence model in artificial intelligence system 258 that can learn without being explicitly programmed. Machine learning model 310 can learn based on data input into machine learning model 310.

Machine learning model 310 can learn using various types of machine learning algorithms. The machine learning algorithms include at least one of a supervised learning, an unsupervised learning, a feature learning, a sparse dictionary learning, and anomaly detection, association rules, or other types of learning algorithms. Examples of machine learning models include an artificial neural network, a decision tree, a support vector machine, a Bayesian network, a genetic algorithm, and other types of models. These machine learning models can be trained using training data to process input data to provide a desired output.

In this illustrative example, search manager 214 can generate, using machine learning model 310, candidate search terms 312 in response to receiving selected document 302 as input document 314. As depicted, input document 314 can be received in user input 316 received from input system 220.

As depicted, search manager 214 can display the set of candidate search terms 312 in graphical user interface 222 on display system 218 in human machine interface 216. Candidate search terms 312 can be all or a subset of search terms identified by machine learning model 310 that are candidates for use. For example, machine learning model 310 can also identify a confidence level at which a candidate search term is sufficiently related to a key term in input document 314. For example, candidate search terms 312 can be the five search terms having a highest confidence level in the search terms identified by machine learning model 310.

In one illustrative example, candidate search terms 312 can be suggestions of search terms that can be used to search for other documents that can be cited as a reference by input document 314. For example, when input document 314 is a criteria document, the search terms can be used to identify other criteria documents that may be cited within the criteria document.

Figure 4:
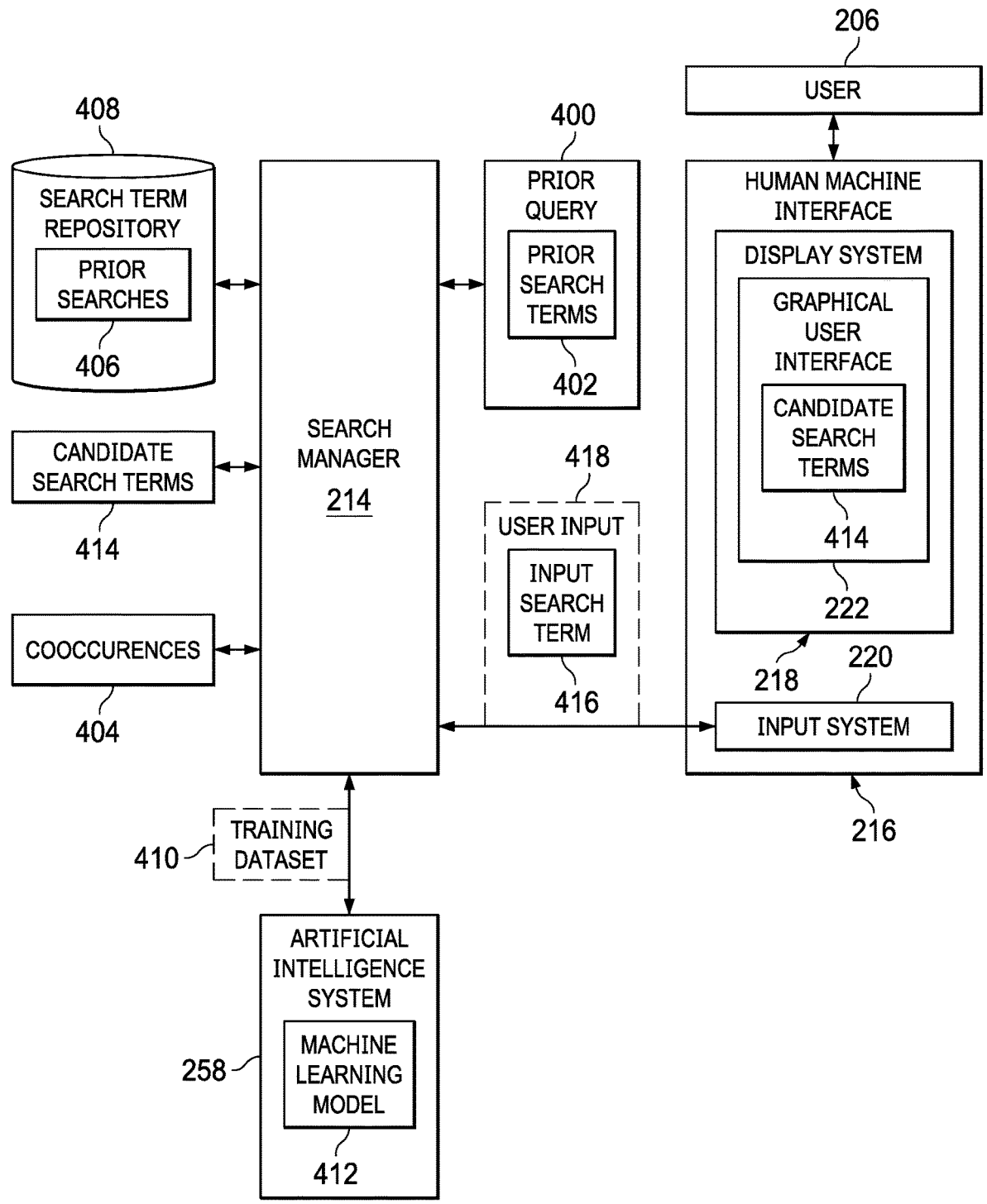
FIG. 4 is another dataflow for generating or suggesting search terms in accordance with an illustrative embodiment.

Turning now to FIG. 4, another dataflow for generating or suggesting search terms is depicted in accordance with an illustrative embodiment. In this illustrative example, search manager 214 can identify prior query 400 comprising prior search terms 402. Search manager 214 determines cooccurrences 404 of prior search terms 402 in which cooccurrences 404 of each prior search term with a number of other prior search terms in prior query 400 comprises how many times a prior search term was used in prior searches 406 in search term repository 408, and how many times each of the number of other prior search terms were used in prior searches 406 with the prior search term in search term repository 408. In this illustrative example, search term repository 408 is a location in which prior searches can be stored. In this illustrative example, prior searches 406 are searches that were previously made to the collection of documents for which candidate search terms 414 are to be suggested for a current search.

Search manager 214 can store prior query 400 and cooccurrences 404 of each prior search term with a number of other prior search terms in prior query 400 in training dataset 410. This process can be repeated any number of times to generate a desired number of samples for training dataset 410. Search manager 214 can train machine learning model 412 to generate candidate search terms 414 from input search term 416. In this illustrative example, input search term 416 is a search term that is entered by user 206 to perform a search. As depicted, input search term 416 can be located in user input 418 received from input system 220.

In the illustrative example, the candidate search terms can be, for example, search terms that are considered to be similar or related enough to be suggested for searching. Candidate search terms 414 can be terms other than synonyms.

As depicted, search manager 214 can generate, by machine learning model 412, candidate search terms 414 in response to receiving input search term 416. Candidate search terms 414 can be all or a subset of the search terms identified by machine learning model 412 as possible candidates for use in searching. Search manager 214 can display candidate search terms 414 in graphical user interface 222 on display system 218 in human machine interface 216. In this manner, search manager 214 can actively suggest search terms for use in searching documents in an interactive manner. For example, the identification of candidate search terms 414 can be generated and displayed each time user 206 inputs a search term into graphical user interface 222. This identification can be made for each search term.

In one illustrative example, one or more technical solutions are present that overcome a technical problem with increasing the usefulness of search results. As a result, one or more technical solutions may provide a technical effect of generating search results that provide more information than currently available with current techniques for searching and displaying search results.

Computer system 212 can be configured to perform at least one of the steps, operations, or actions described in the different illustrative examples using software, hardware, firmware, or a combination thereof. As a result, computer system 212 operates as a special purpose computer system in which search manager 214 in computer system 212 enables searching for documents in a manner that takes into account the relevancy of search terms within the document with respect to a collection of documents searched. In particular, search manager 214 transforms computer system 212 into a special purpose computer system as compared to currently available general computer systems that do not have search manager 214.

In the illustrative example, the use of search manager 214 in computer system 212 integrates processes into a practical application for searching for documents that increases the performance of computer system 212. In other words, search manager 214 in computer system 212 is directed to a practical application of processes integrated into search manager 214 in computer system 212 that performs a search on a collection of documents in which a separate search is performed for each search term received in a query. Scores are received in which the scores indicate the importance of the search term to a document in the collection of documents searched using the search term. The scores are combined to form aggregate scores for the documents based on the scores returned in the searches. The documents can be ranked and displayed on the display system. The display can take the form of a graphical display that indicates the aggregate score. Further, the display can also be a graphical display that indicates the scores of individual terms.

The illustration of search environment 200 in FIG. 2 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although repository 208 is shown as being located outside of the block for document search system 210 and computer system 212, repository 208 can be considered part of document search system 210 in some illustrative examples. Repository 208 can be located in computer system 212 in document search system 210. In other illustrative examples, repository 208 can be located in another computer system outside of document search system 210.

In the illustrative example, user 206 is described with respect to a person. In other illustrative examples, user 206 can be a non-human entity such as an application, a software program, program code, an artificial intelligence system, a machine learning model, or some other computer-implemented process. When user 206 is a non-human entity, user 206 can generate user input 316 without using human machine interface 216.

In another illustrative example, search manager 214 can calculate scores 234 instead of receiving scores 234 from backend 207. For example, search manager 214 can calculate scores 234 for documents 202 for collection of documents 204 in repository 208. Scores 234 can be stored in a data structure such as a file, a linked list, a database, or some other data structure suitable for a desired level of performance.

In still another illustrative example, one or more collections of documents can be present in addition to collection of documents 204 in repository 208 and can be located in other repositories. These collections of documents can be searched along with collection of documents 204. In other illustrative examples, a user input can select which collection of documents should be searched.

Figure 5:
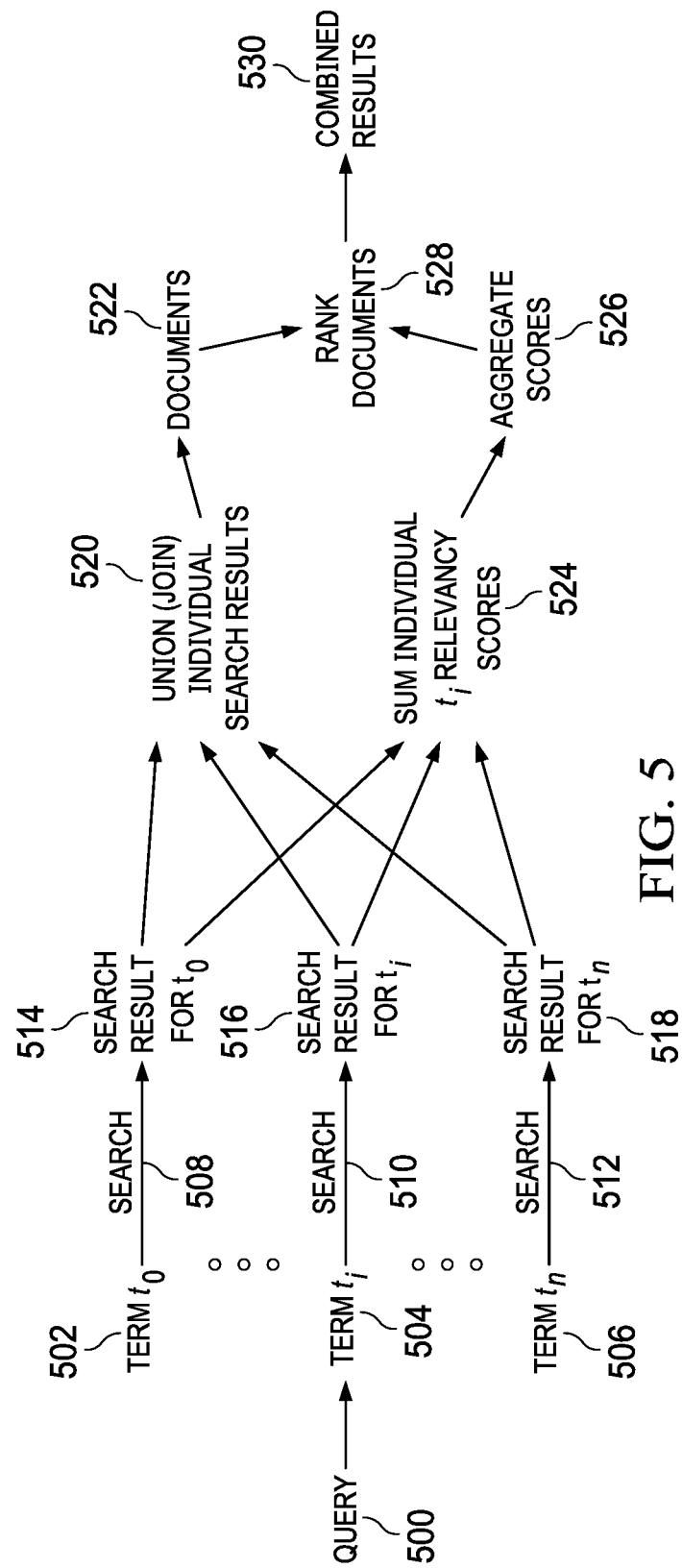
FIG. 5 is a dataflow for generating a search result in accordance with an illustrative embodiment.

With reference next to FIG. 5, a dataflow for generating a search result is depicted in accordance with an illustrative embodiment. This data flow can be implemented in document search system 210 in FIG. 2. In particular, this process can be implemented using search manager 214 in document search system 210.

As depicted, query 500 includes term 502, term 504, and term 506. Query 500 is an example of query 226 in FIG. 2. These terms identified are in query 500. An individual search is performed for each of these terms in query 500. As depicted, search 508 is performed for term 502; search 510 is performed for term 504; and search 512 is performed for term 506. Each of the searches is performed on the same collection of documents.

Each of the searches returns a search result. For example, search 508 returns search result 514; search 510 returns search result 516; and search 512 returns search result 518. In this illustrative example, each search result contains documents. Some of the documents made are duplicated in other search results and other documents are unique within the search results. As a result, union of individual search results 520 is performed to identify documents 522.

Further, the search results include scores associated with the documents. These scores are also referred to as relevancy scores. In other words, each document returned in a search result includes a score as to the importance of the search term to the documents in the document search. Sum relevancy scores 524 is performed on the search results to generate aggregate scores 526. For example, when a document is present in more than one of the search results, the relevancy score for that document is added to form aggregate scores 526 for the documents. Aggregate scores 526 can be associated with sum relevancy scores 524 to perform rank documents 528.

Rank documents 528 is performed on documents 522 in which documents 522 are ranked using aggregate scores 526 associated with documents 522. The result of rank documents 528 is combined results 530. Combined results 530 is an example of combined results 244 in FIG. 2.

The illustration of the dataflow in generating combined results 530 is intended as an example of one manner in which combined results 530 can be generated. This example is not meant to limit the manner in which other illustrative examples can be implemented. For example, other queries can include other numbers of terms in place of the three terms, term 502, term 504, and term 506, in this example. Other queries can include two terms, nine terms, 15 terms, or some other number of terms.

Turning next to FIGS. 6-9, illustrations of displays in a graphical user interface for a search system are depicted in accordance with illustrative embodiments. The different displays in these figures are examples of displays that can be displayed within graphical user interface 222 on display system 218 in document search system 210 in FIG. 2.

Figure 6:
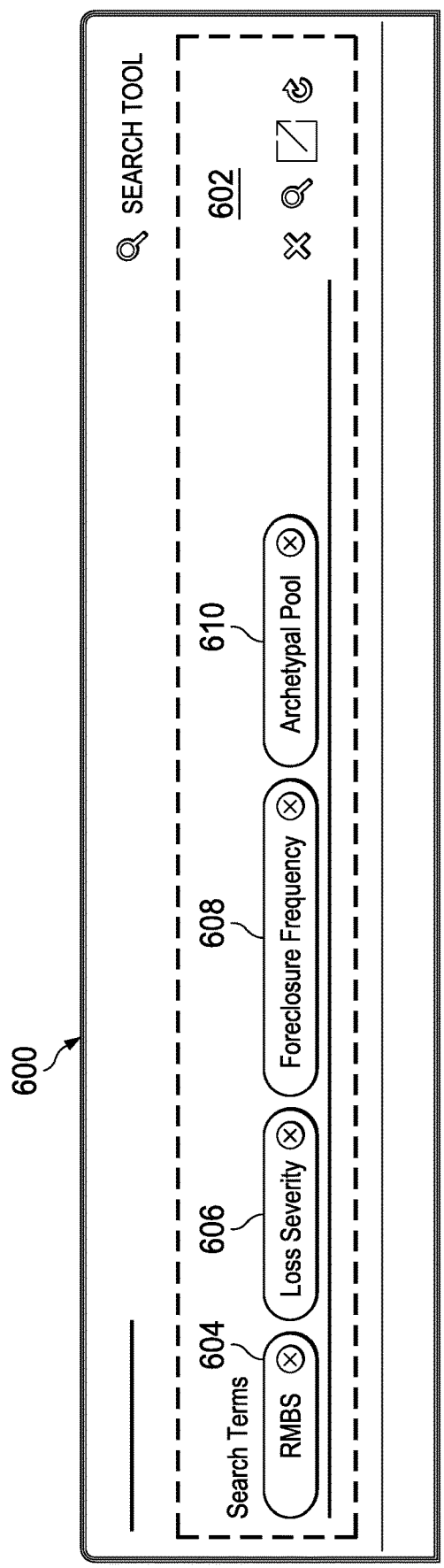
FIG. 6 is an illustration of a display of a search interface in accordance with an illustrative embodiment.

With reference first to FIG. 6, an illustration of a display of a search interface is depicted in accordance with an illustrative embodiment. In this illustrative example, search interface 600 is an example of an interface in which a user can enter search terms to form a query to search for documents. In this illustrative example, search terms can input in section 602. In this illustrative example, search terms include RMBS 604, Loss Severity 606, Foreclosure Frequency 608, and Archetypal Pool 610.

With reference now to FIG. 7, an illustration of search results is depicted in accordance with an illustrative embodiment. As depicted, search results 700 are displayed in search interface 600. The search results are generated in response to the search terms entered into section 602. In this display of search interface 600, search results 700 comprise the top ten search results out of 92 results. In this illustrative example, search results 700 are displayed in a ranked order based on aggregate scores for the documents returned in a search.

With reference next to FIG. 8, an illustration of search results including a heat map is depicted in accordance with an illustrative embodiment. In this illustrative example, search interface 600 displays search results 800 with heat map 802. As depicted, search results 800 are displayed based on a rank that is determined using the aggregate scores that have been aggregated from individual scores for terms in the documents returned in a search.

In this illustrative example, heat map 802 has cells 803 arranged in rows 804 and columns 806. As depicted, rows 804 correspond to search results 800. In other words, each row in heat map 802 corresponds to a search result in search results 800.

In this illustrative example, column 808 contains aggregate scores for search results 800. Each aggregate score in column 808 is an aggregate score for a search result in search results 800. For example, aggregate score 811 is the aggregate score for search result 810 in search results 800.

Column 814, column 816, column 818, and column 820 in columns 806 correspond to search terms RMBS, Loss Severity, Foreclosure Frequency, and Archetypal Pool, respectively. These are the search terms used to perform the search that returned search results 800. The values in these columns represent the scores for each of the search terms with respect to a document in search results 800.

In this illustrative example, cells 803 contain scores displayed in graphical association with graphical indicators. As depicted, these graphical indicators provide a graphical indication of the scores for the combined score and the scores for individual search terms relative to each other.

The particular color selected for the graphical indicator can be based on thresholds for the scores. For example, a threshold for a color can be a range of values for a score. For example, if the score can be values from 1.0 to 20, one color can be assigned a range of 1.0-5.0. A second color can be assigned to a range of 5.1-10.0 A third color can be assigned to a range of 10.1-13.5. A fourth color can be assigned to a range of 13.6-17.0, and a fifth color can be assigned to a range of 17.1-20. A color can be assigned to a document by identifying the range in which the score falls. In other illustrative examples, other numbers of colors and other ranges can be used.

In this illustrative example, graphical indicators take the form of color. In other illustrative examples, the graphical indicators can take other forms. For example, a graphical indicator can include at least one of at least one of an icon, a pictogram, an ideogram, a graphic, an image, text, an animation, bolding, a line, an arrow, or some other suitable graphic.

Turning now to FIG. 9, another illustration of search results including a heat map is depicted in accordance with an illustrative embodiment. In this illustrative example, search results 800 and heat map 802 are displayed in a configuration based on the search term "RMBS." The selection of the search term results in search results 800 being displayed in a ranked order based on the scores for RMBS as shown in column 814. In this manner, a user can view documents in search results 800 based on the scores of individual search terms in addition to viewing search results 800 based on the aggregate scores in column 808.

The illustration of search interface 600 in FIGS. 6-9 are presented for presenting one illustrative example. The display is not meant to limit the manner in which other illustrative examples can be implemented. For example, other illustrative examples can display a heat map using other colors or graphical indicators. In other words, heat map 802 can use graphical icons displayed within cells 803 to identify which cells in cells 803 have higher scores or lower scores relative to other cells in cells 803.

Additionally, other types of graphical displays can be used in addition to or in place of a heat map. For example, other types of graphical displays include a 100 percent stacked bar column, a stacked bar column, an order column, or a stacked area. A 100 percent stacked bar column shows the importance a term has today for a ranking score without differentiating between raw magnitude scores. A stacked bar column can show the influence of an individual score on the aggregate score. Further, this type of graphical display can also show the raw difference between different documents in their components. An order column is a ranked bar column by aggregate scores. A stacked area is another type of visual display that provides a visual representation of information similar to a 100 percent stacked bar column or stacked bar column using areas instead of bars.

Figure 10:
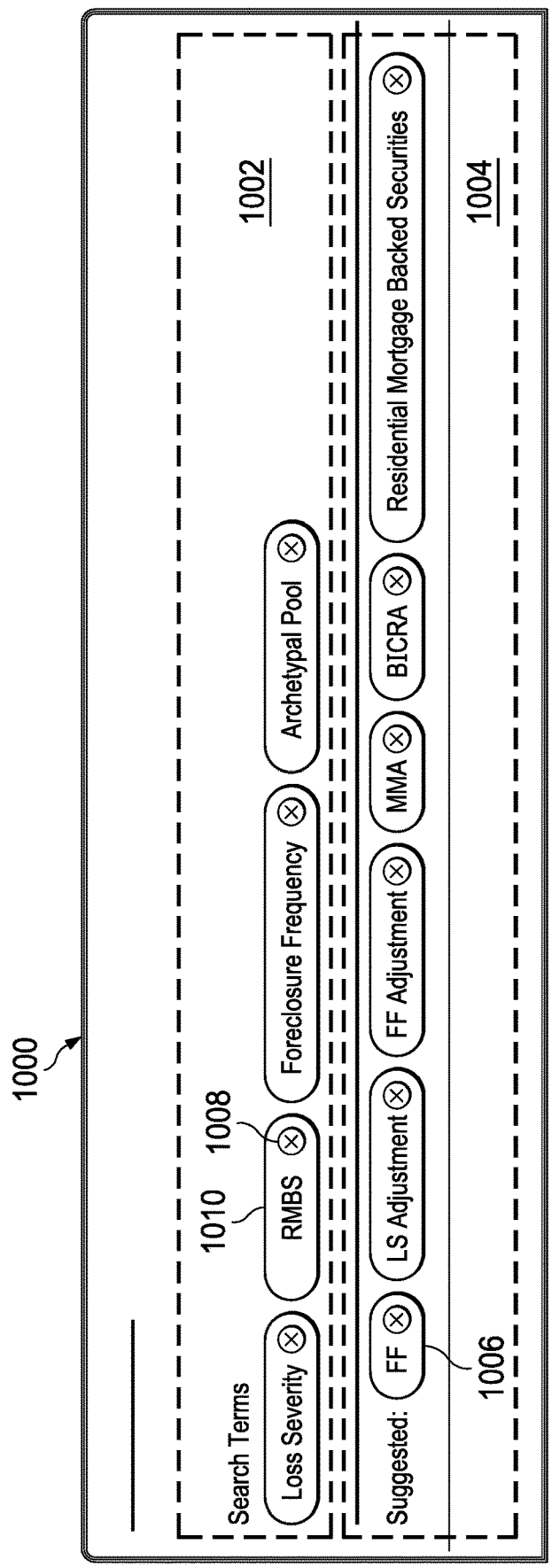
FIG. 10 is an illustration of a search interface including search term suggestions in accordance with an illustrative embodiment.

Turning next to FIG. 10, an illustration of a search interface including search term suggestions is depicted in accordance with an illustrative embodiment. In this illustrative example, search interface 1000 is an example of a display that can be displayed within graphical user interface 222 on display system 218 in document search system 210 in FIG. 2. In this illustrative example, search interface 1000 includes input section 1002 in which search terms can be entered through user input. Suggestion section 1004 in search interface 1000 displays suggested candidate search terms that may be used in the search. A user input selecting a candidate search term displayed in suggestion section 1004 can cause the selected candidate search terms to be added to the search terms in input section 1002. For example, a user can double-click on search term FF 1006 and cause that candidate search term to be moved to input section 1002.

Additionally, the search terms in both input section 1002 and suggestion section 1004 can be with a different user input. For example, a selection of the graphical "X" 1008 in search term RMBS 1010 causes that search term to be removed from input section 1002. The display of search interface 1000 is an example of one manner in which a user input can be received. The display of search interface 1000 in this figure is not meant to limit the manner in which search interface 1000 can be implemented in other illustrative examples.

Figure 11:
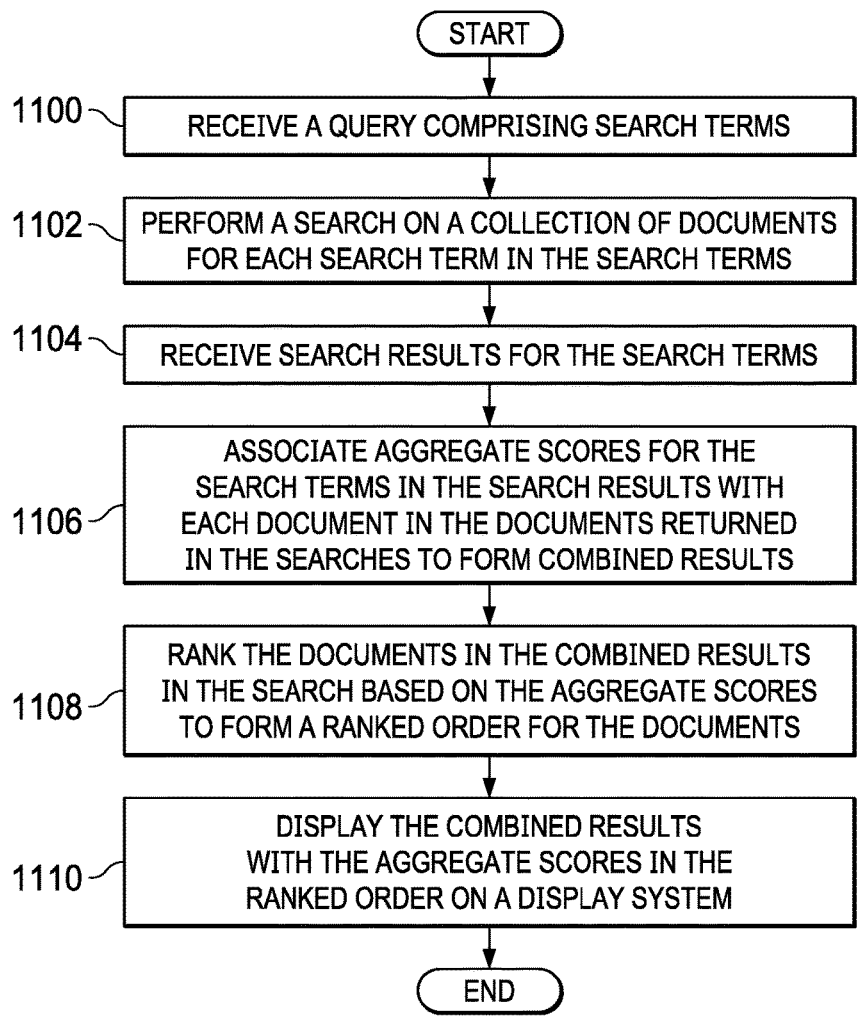
FIG. 11 is a flowchart of a process for searching for documents in accordance with an illustrative embodiment.

Turning next to FIG. 11, a flowchart of a process for searching for documents is depicted in accordance with an illustrative embodiment. The process in FIG. 11 can be implemented in hardware, software, or both. When implemented in software, the process can take the form of program code that is run by one of more processor units located in one or more hardware devices in one or more computer systems. For example, the process can be implemented in search manager 214 in computer system 212 in FIG. 2.

The process begins by receiving a query comprising search terms (step 1100). The process performs a search on a collection of documents for each search term in the search terms (step 1102).

The process receives search results for the search terms (step 1104). In step 1104, each search result includes documents from the collection of documents containing a search term in the search terms and scores associated with the documents. A score in the scores indicates an importance of the search term to a document in the collection of documents searched using the search term.

The process associates aggregate scores for the search terms in the search results with each document in the documents returned in the searches to form combined results (step 1106). In step 1106, a combined result in the combined results comprises the document and an aggregate score associated with the document. The process ranks the documents in the combined results in the search based on the aggregate scores to form a ranked order for the documents (step 1108).

The process displays the combined results with the aggregate scores in the ranked order on a display system (step 1110). The process terminates thereafter.

Figure 12:
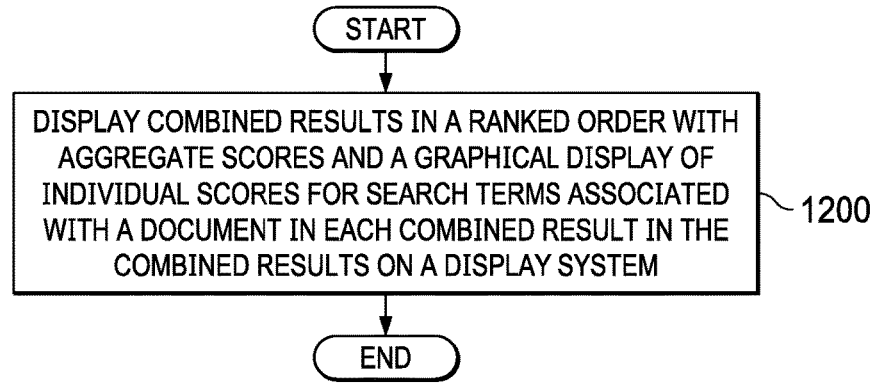
FIG. 12 is a flowchart of a process for displaying combined results in accordance with an illustrative embodiment.

With reference next to FIG. 12, a flowchart of a process for displaying combined results is depicted in accordance with an illustrative embodiment. The process in FIG. 12 is an example of one implementation for step 1108 in FIG. 11.

The process displays combined results in a ranked order with aggregate scores and a graphical display of individual scores for search terms associated with a document in each combined result in the combined results on a display system (step 1200). The process terminates thereafter. In step 1200, the graphical display comprises a heat map.

Figure 13:
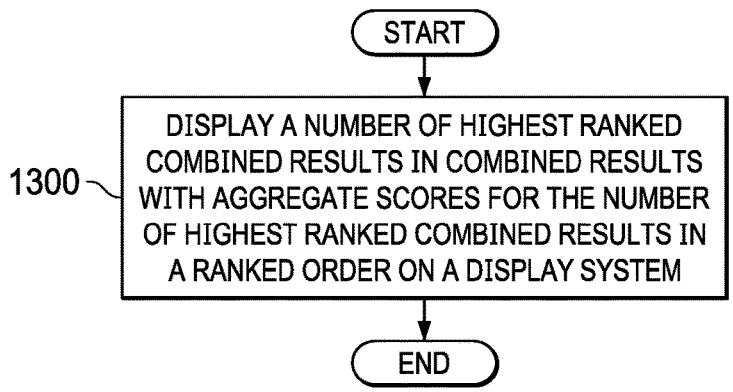
FIG. 13 is a flowchart of a process for displaying combined results in accordance with an illustrative embodiment.

With reference to FIG. 13, a flowchart of a process for displaying combined results is depicted in accordance with an illustrative embodiment. The process in FIG. 13 is an example of one implementation for step 1108 in FIG. 11.

The process displays a number of highest ranked combined results in combined results with aggregate scores for the number of highest ranked combined results in a ranked order on a display system (step 1300). The process terminates thereafter.

Figure 14:
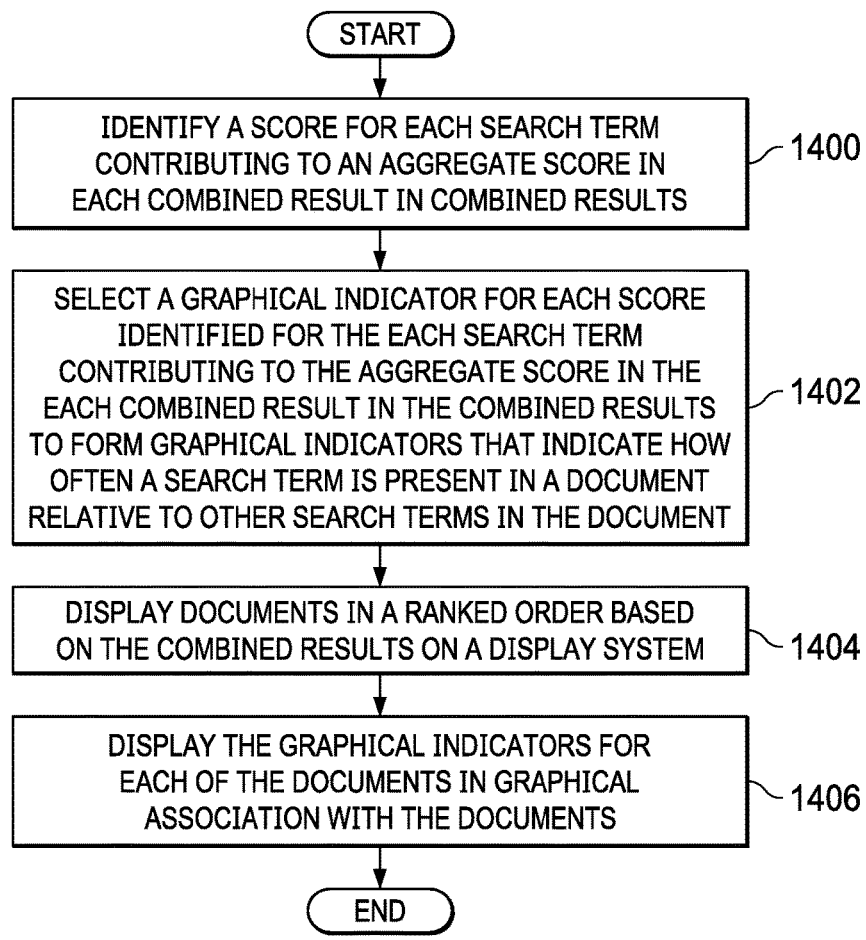
FIG. 14 is a flowchart of a process for displaying combined results in accordance with an illustrative embodiment.

Turning now to FIG. 14, a flowchart of a process for displaying combined results is depicted in accordance with an illustrative embodiment. The process in FIG. 14 is an example of one implementation for step 1200 in FIG. 12.

The process begins by identifying a score for each search term contributing to an aggregate score in each combined result in the combined results (step 1400). The process selects a graphical indicator for each score identified for each search term contributing to the aggregate score in each combined result in the combined results to form graphical indicators that indicate how often a search term is present in a document relative to other search terms in the document (step 1402).

The process displays documents in a ranked order based on the combined results on a display system (step 1404). The process displays the graphical indicators for each of the documents in graphical association with the documents (step 1406). The process terminates thereafter.

Figure 15:
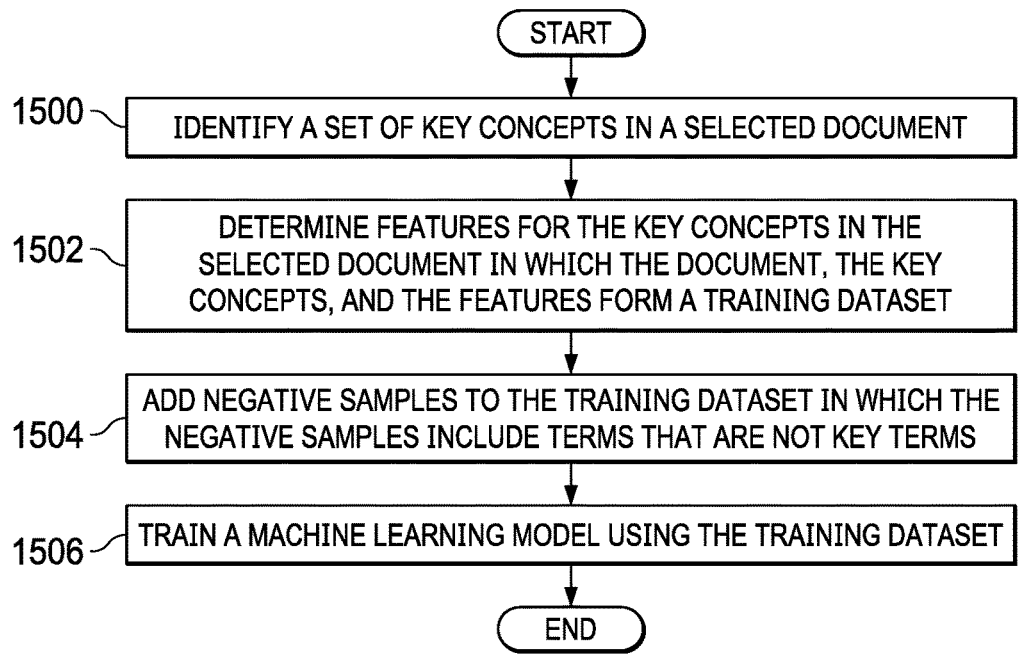
FIG. 15 is a flowchart of a process for training a machine learning model to identify candidate search terms in accordance with an illustrative embodiment.

Turning now to FIG. 15, a flowchart of a process for training a machine learning model to identify candidate search terms is depicted in accordance with an illustrative embodiment. The process in FIG. 15 can be implemented in hardware, software, or both. When implemented in software, the process can take the form of program code that is run by one or more processor units located in one or more hardware devices in one or more computer systems. For example, the process can be implemented in search manager 214 in computer system 212 in FIG. 2.

The process begins by identifying a set of key concepts in a selected document (step 1500). The process determines features for the key concepts in the selected document in which the document, the key concepts, and the features form a training dataset (step 1502).

The process adds negative samples to the training dataset in which the negative samples include terms that are not key terms (step 1504).

The process trains a machine learning model using the training dataset (step 1506). The process terminates thereafter. In step 1506, the machine learning model is trained to determine an importance of search terms from an input document and recommend a set of the candidate search terms based on the importance of the candidate search terms.

Figure 16:
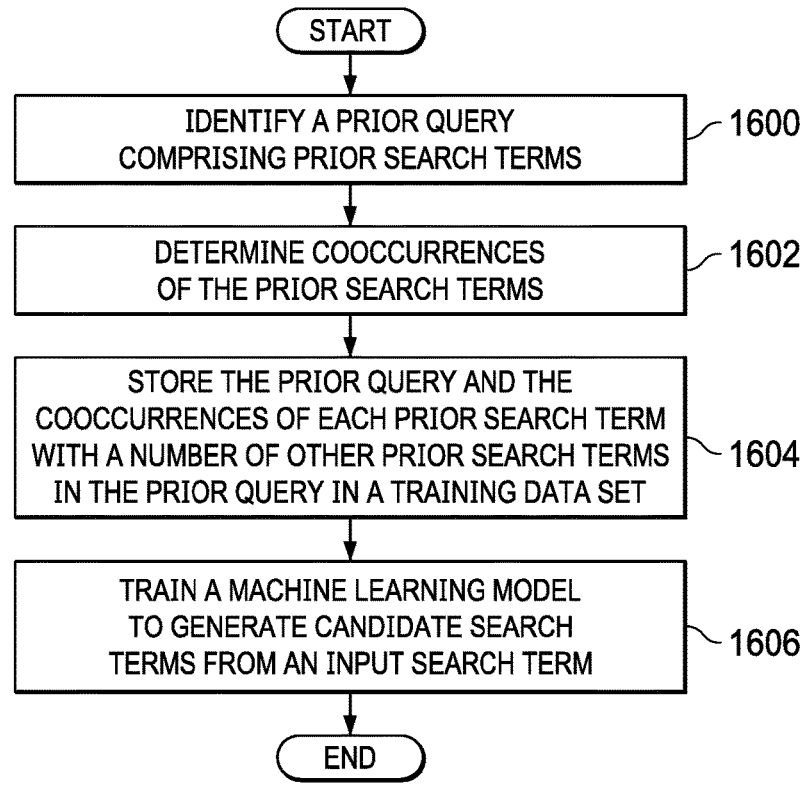
FIG. 16 is a flowchart of a process for training a machine learning model to generate candidate search terms in accordance with an illustrative embodiment.

Turning now to FIG. 16, a flowchart of a process for training a machine learning model to generate candidate search terms is depicted in accordance with an illustrative embodiment. The process in FIG. 16 can be implemented in hardware, software, or both. When implemented in software, the process can take the form of program code that is run by one or more processor units located in one or more hardware devices in one or more computer systems. For example, the process can be implemented in search manager 214 in computer system 212 in FIG. 2.

The process begins by identifying a prior query comprising prior search terms (step 1600). The process determines cooccurrences of the prior search terms (step 1602). In step 1602, the cooccurrences of each prior search term with a number of other prior search terms in the query comprises how many times a prior search term was used in prior searches in a search term repository, and how many times each of the number of other prior search terms was used in the prior searches with the prior search term in the search term repository. The process stores the prior query and the cooccurrences of each prior search term with a number of other prior search terms in the prior query in a training data set (step 1604). The process trains a machine learning model to generate candidate search terms from an input search term (step 1606). The process terminates thereafter.

The flowcharts and block diagrams in the different depicted embodiments illustrate the architecture, functionality, and operation of some possible implementations of apparatuses and methods in an illustrative embodiment. In this regard, each block in the flowcharts or block diagrams can represent at least one of a module, a segment, a function, or a portion of an operation or step. For example, one or more of the blocks can be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram.

For example, step 1504 in FIG. 15 is an optional step. This step may be omitted in some illustrative examples.

Figure 17:
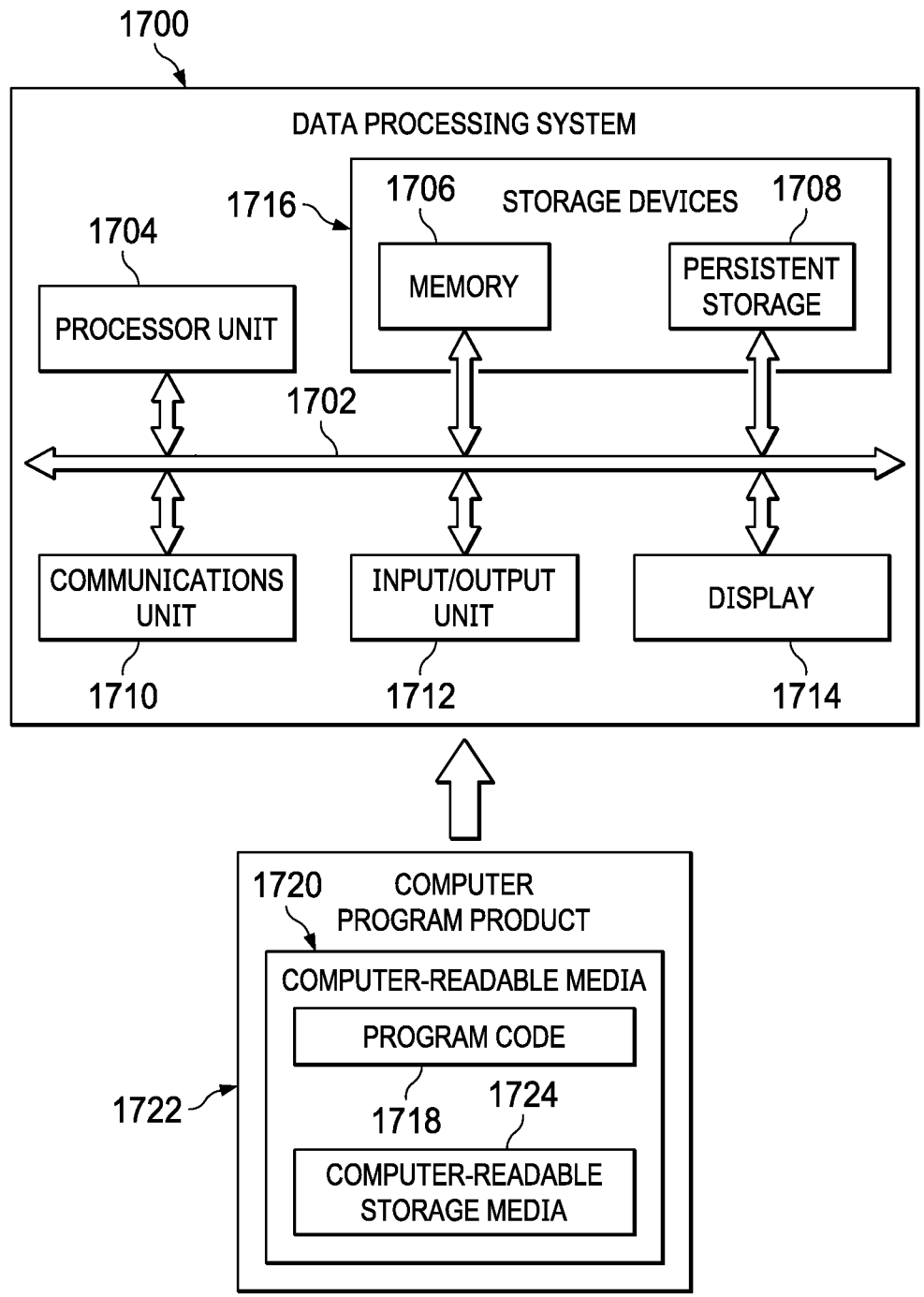
FIG. 17 is a block diagram of a data processing system in accordance with an illustrative embodiment.

Turning now to FIG. 17, a block diagram of a data processing system is depicted in accordance with an illustrative embodiment. Data processing system 1700 can be used to implement server computer 104, server computer 106, client devices 110, in FIG. 1. Data processing system 1700 can also be used to implement computer system 212 in FIG. 2. In this illustrative example, data processing system 1700 includes communications framework 1702, which provides communications between processor unit 1704, memory 1706, persistent storage 1708, communications unit 1710, input/output (I/O) unit 1712, and display 1714. In this example, communications framework 1702 takes the form of a bus system.

Processor unit 1704 serves to execute instructions for software that can be loaded into memory 1706. Processor unit 1704 includes one or more processors. For example, processor unit 1704 can be selected from at least one of a multicore processor, a central processing unit (CPU), a graphics processing unit (GPU), a physics processing unit (PPU), a digital signal processor (DSP), a network processor, or some other suitable type of processor. Further, processor unit 1704 can may be implemented using one or more heterogeneous processor systems in which a main processor is present with secondary processors on a single chip. As another illustrative example, processor unit 1704 can be a symmetric multi-processor system containing multiple processors of the same type on a single chip.

Memory 1706 and persistent storage 1708 are examples of storage devices 1716. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1716 may also be referred to as computer-readable storage devices in these illustrative examples. Memory 1706, in these examples, can be, for example, a random-access memory or any other suitable volatile or non-volatile storage device. Persistent storage 1708 may take various forms, depending on the particular implementation.

For example, persistent storage 1708 may contain one or more components or devices. For example, persistent storage 1708 can be a hard drive, a solid-state drive (SSD), a flash memory, a rewritable optical disk, a rewritable magnetic tape, or some combination of the above. The media used by persistent storage 1708 also can be removable. For example, a removable hard drive can be used for persistent storage 1708.

Communications unit 1710, in these illustrative examples, provides for communications with other data processing systems or devices. In these illustrative examples, communications unit 1710 is a network interface card.

Input/output unit 1712 allows for input and output of data with other devices that can be connected to data processing system 1700. For example, input/output unit 1712 may provide a connection for user input through at least one of a keyboard, a mouse, or some other suitable input device. Further, input/output unit 1712 may send output to a printer. Display 1714 provides a mechanism to display information to a user.

Instructions for at least one of the operating system, applications, or programs can be located in storage devices 1716, which are in communication with processor unit 1704 through communications framework 1702. The processes of the different embodiments can be performed by processor unit 1704 using computer-implemented instructions, which may be located in a memory, such as memory 1706.

These instructions are referred to as program code, computer usable program code, or computer-readable program code that can be read and executed by a processor in processor unit 1704. The program code in the different embodiments can be embodied on different physical or computer-readable storage media, such as memory 1706 or persistent storage 1708.

Program code 1718 is located in a functional form on computer-readable media 1720 that is selectively removable and can be loaded onto or transferred to data processing system 1700 for execution by processor unit 1704. Program code 1718 and computer-readable media 1720 form computer program product 1722 in these illustrative examples. In the illustrative example, computer-readable media 1720 is computer-readable storage media 1724.

In these illustrative examples, computer-readable storage media 1724 is a physical or tangible storage device used to store program code 1718 rather than a medium that propagates or transmits program code 1718. Computer readable storage media 1724, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Alternatively, program code 1718 can be transferred to data processing system 1700 using a computer-readable signal media. The computer-readable signal media can be, for example, a propagated data signal containing program code 1718. For example, the computer-readable signal media can be at least one of an electromagnetic signal, an optical signal, or any other suitable type of signal. These signals can be transmitted over connections, such as wireless connections, optical fiber cable, coaxial cable, a wire, or any other suitable type of connection.

Further, as used herein, "computer-readable media 1720" can be singular or plural. For example, program code 1718 can be located in computer-readable media 1720 in the form of a single storage device or system. In another example, program code 1718 can be located in computer-readable media 1720 that is distributed in multiple data processing systems. In other words, some instructions in program code 1718 can be located in one data processing system while other instructions in program code 1718 can be located in one data processing system. For example, a portion of program code 1718 can be located in computer-readable media 1720 in a server computer while another portion of program code 1718 can be located in computer-readable media 1720 located in a set of client computers.

The different components illustrated for data processing system 1700 are not meant to provide architectural limitations to the manner in which different embodiments can be implemented. The different illustrative embodiments can be implemented in a data processing system including components in addition to or in place of those illustrated for data processing system 1700. Other components shown in FIG. 17 can be varied from the illustrative examples shown. The different embodiments can be implemented using any hardware device or system capable of running program code 1718.

The description of the different illustrative embodiments has been presented for purposes of illustration and description and is not intended to be exhaustive or limited to the embodiments in the form disclosed. In some illustrative examples, one or more of the components may be incorporated in or otherwise form a portion of, another component. For example, memory 1706, or portions thereof, may be incorporated in processor unit 1704 in some illustrative examples.

Thus, the illustrative embodiments provide a method, apparatus, system, and computer program product for searching for documents. In one illustrative example, a method searches for documents. A query comprising search terms is received by the computer system. A search is performed by the computer system on a collection of documents for each search term in the search terms. Search results are received by the computer system for the search terms. Each search result includes documents from the collection of documents containing a search term in the search terms and scores associated with the documents. A score in the scores indicates an importance of the search term to a document in the collection of documents searched using the search term. Aggregate scores for the search terms in the search results are associated by the computer system with each document in the documents returned in the searches to form combined results in which a combined result in the combined results comprises the document and an aggregate score associated with the document. The documents in the combined results in the search are ranked by the computer system based on the aggregate scores to form a ranked order for the documents. The combined results with the aggregate scores in the ranked order are displayed on a display system by the computer system.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component can be configured to perform the action or operation described. For example, the component can have a configuration or design for a structure that provides the component an ability to perform the action or operation that is described in the illustrative examples as being performed by the component. Further, To the extent that terms "includes", "including", "has", "contains", and variants thereof are used herein, such terms are intended to be inclusive in a manner similar to the term "comprises" as an open transition word without precluding any additional or other elements.

Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A document search system comprising:
   a computer system; and
   a search manager in the computer system, wherein the search manager is configured to:
   receive a query comprising search terms;
   perform a search on a collection of documents for each search term in the search terms;
   receive search results for each search term, wherein each search result includes documents from the collection of documents containing the search term in question and scores associated with the documents, wherein a score in the scores indicates an importance of the search term to each document in the collection of documents searched using the search term;
   associate aggregate scores for the search terms in the search results with the documents returned in the searches to form combined results in which a combined result in the combined results comprises the document in the documents and an aggregate score associated with the document;
   rank the documents in the combined results in the search based on the aggregate scores to form a ranked order for the documents; and
   display, on a display system, the combined results with the aggregate scores in the ranked order and a graphical display of individual scores for the search terms associated with the document in each combined result in the combined results, wherein the graphical display comprises a heat map displaying a rank of each search result in the search results.

2. The document search system of claim 1, wherein in displaying, on the display system, the combined results with the aggregate scores in the ranked order, the search manager is configured to:
   display, on the display system, a number of highest ranked combined results in the combined results with the aggregate scores for the number of highest ranked combined results in the ranked order.

3. The document search system of claim 1, wherein in displaying, on the display system, the combined results in the ranked order with the aggregate scores and a graphical display of individual scores for the search terms associated with the document in each combined result in the combined results, the search manager is configured to:
   identify a score for each search term contributing to an aggregate score in each combined result in the combined results;
   select a graphical indicator for each score identified for each search term contributing to the aggregate score in each combined result in the combined results to form graphical indicators that indicate how often the search term is present in a document relative to other search terms in the document, wherein the graphical indicator comprises one of a color, an icon, a pictogram, an ideogram, an image, text, animation, bolding, a line, or an arrow;
   display the documents in a ranked order based on the combined results; and
   display the graphical indicators for each of the documents in graphical association with the documents.

4. The document search system of claim 3, wherein in displaying the graphical indicators for each of the documents in a graphical association with the documents, the search manager is configured to:
   display the graphical indicators for each of the documents in the graphical association with the documents as a heat map.

5. The document search system of claim 1, wherein the search manager is configured to:
   compute a commonality score for each of the search terms in the document, wherein the commonality score for the search term based on a number of times the search term is present in the document and the number of times the search term is present in all documents subject to the search.

6. The document search system of claim 1, wherein the scores are term frequency-inverse document frequency (tf-idf) scores.

7. The document search system of claim 1, wherein the search manager is configured to:
   identify a set of key terms in a selected document;
   determine features for the key terms in the selected document in which the document, the set of key terms, and the features form a training dataset; and
   train a machine learning model using the training dataset, wherein the machine learning model is trained to determine an importance of candidate search terms from an input document recommend a set of the candidate search terms.

8. The document search system of claim 7, wherein the search manager is configured to:
   add negative samples to the training dataset in which the negative samples include terms that are not key terms.

9. The document search system of claim 7, wherein the search manager is configured to:

generate, by the machine learning model, the candidate search terms in response to receiving the selected document; and display the set of the candidate search terms in a graphical user interface on the display system.

10. The document search system of claim 1, wherein the search manager is configured to:

identify a prior query comprising prior search terms;

determine cooccurrences of the prior search terms in which the cooccurrences of each prior search term with a number of other prior search terms in the prior query comprises how many times a prior search term was used in prior searches in a search term repository and how many times each of the number of other prior search terms was used in the prior searches with the prior search term in the search term repository;

store the prior query and the cooccurrences of each prior search term with a number of other prior search terms in the prior query in a training data set; and train a machine learning model to generate candidate search terms from an input search term.

11. The document search system of claim 10, wherein the search manager is configured to:

generate, by the machine learning model, candidate search terms in response to receiving the input search term; and display the candidate search terms in a graphical user interface on the display system.

12. The document search system of claim 1, wherein in performing the search on a collection of documents for each search term in the search terms, the search manager is configured to:

perform the search on a collection of documents for each search term in the search terms using a fuzzy searching process.

13. A method for searching for documents, the method comprising:

receiving, by a computer system, a query comprising search terms;

performing, by the computer system, a search on a collection of documents for each search term in the search terms;

receive search results for each search term, wherein each search result includes documents from the collection of documents containing the search term in question and scores associated with the documents, wherein a score in the scores indicates an importance of the search term to each document in the collection of documents searched using the search term;

associating, by the computer system, aggregate scores for the search terms in the search results with each document in the documents returned in the searches to form combined results in which a combined result in the combined results comprises the document and an aggregate score associated with the document;

ranking, by the computer system, the documents in the combined results in the search based on the aggregate scores to form a ranked order for the documents; and displaying, by the computer system on a display system, the combined results with the aggregate scores in the ranked order and a graphical display of individual scores for the search terms associated with the document in each combined result in the combined results, wherein the graphical display comprises a heat map displaying a rank of each search result in the search results.

14. The method of claim 13, wherein displaying, on the display system, the combined results with the aggregate scores in the ranked order comprises:

displaying, on the display system, a number of highest ranked combined results in the combined results with the aggregate scores for the number of highest ranked combined results in the ranked order.

15. The method of claim 13, wherein displaying, on the display system, the combined results in the ranked order with the aggregate scores and a graphical display of individual scores for the search terms associated with the document in each combined result in the combined results comprises:

identifying, by the computer system, a score for each search term contributing to an aggregate score in each combined result in the combined results;

selecting, by the computer system, a graphical indicator for each score identified for each search term contributing to the aggregate score in each combined result in the combined results to form graphical indicators that indicate how often the search term is present in the document relative to other search terms in the document, wherein the graphical indicator comprises one of a color, an icon, a pictogram, an ideogram, an image, text, animation, bolding, a line, or an arrow;

displaying, by the computer system, the documents in a ranked order based on the combined results; and displaying, by the computer system, the graphical indicators for each of the documents in graphical association with the documents.

16. The method of claim 15, wherein displaying, by the computer system, the graphical indicators for each of the documents in a graphical association with the documents comprises:

displaying, by the computer system, the graphical indicators for each of the documents in the graphical association with the documents as a heat map.

17. The method of claim 13, wherein the scores are term frequency-inverse document frequency (tf-idf) scores.

18. The method of claim 13 further comprising:

identifying, by the computer system, a set of key concepts in a selected document;

determining, by the computer system, features for the key concepts in the selected document in which the document, the key concepts, and the features form a training dataset; and training, by the computer system, a machine learning model using the training dataset, wherein the machine learning model is trained to determine an importance of candidate search terms from an input document recommend a set of the candidate search terms.

19. The method of claim 18 further comprising:

adding, by the computer system, negative samples to the training dataset in which the negative samples include terms that are not key terms.

20. The method of claim 18 further comprising:

generating, by the machine learning model, the candidate search terms in response to receiving the selected document; and displaying, by the computer system, the set of the candidate search terms in a graphical user interface on the display system.

21. The method of claim 13 further comprising:

identifying, by the computer system, a prior query comprising prior search terms;

determining, by the computer system, cooccurrences of the prior search terms in which the cooccurrences of each prior search term with a number of other prior search terms in the query comprises how many times a prior search term was used in prior searches in a search term repository and how many times each of the number of other prior search terms was used in the prior searches with the prior search term in the search term repository;

storing, by the computer system, the prior query and the cooccurrences of each prior search term with a number of other prior search terms in the prior query in a training data set; and training, by the computer system, a machine learning model to generate candidate search terms from an input search term.

22. The method of claim 21 further comprising:

generating, by the machine learning model, candidate search terms in response to receiving the input search term; and displaying, by the computer system, the candidate search terms in a graphical user interface on the display system.

23. The method of claim 13, wherein performing, by the computer system, the search on a collection of documents for each search term in the search terms comprises:

performing, by the computer system, the search on a collection of documents for each search term in the search terms using a fuzzy searching process.

24. A computer program product for searching for documents, the computer program product comprising:

a computer-readable storage media;

first program code, stored on the computer-readable storage media, executable by a computer system to cause the computer system to receive a query comprising search terms;

second program code, stored on the computer-readable storage media, executable by the computer system to cause the computer system to perform a search on a collection of documents for each search term in the search terms;

third program code, stored on the computer-readable storage media, executable by the computer system to cause the computer system to receive search results for each search term, wherein each search result includes documents from the collection of documents containing the search term in question and scores associated with the documents, wherein a score in the scores indicates an importance of the search term to each document in the collection of documents searched using the search term;

fourth program code, stored on the computer-readable storage media, executable by the computer system to cause the computer system to associate aggregate scores for the search terms in the search results with the documents returned in the searches to form combined results in which a combined result in the combined results comprises the document in the documents and an aggregate score associated with the document;

fifth program code, stored on the computer-readable storage media, executable by the computer system to cause the computer system to rank the documents in the combined results in the search based on the aggregate scores to form a ranked order for the documents; and sixth program code, stored on the computer-readable storage media, executable by the computer system to cause the computer system to display, on a display system, the combined results with the aggregate scores in the ranked order and a graphical display of individual scores for the search terms associated with the document in each combined result in the combined results, wherein the graphical display comprises a heat map displaying a rank of each search result in the search results.

25. The computer program product of claim 24, wherein the sixth program code comprises:

program code, stored on the computer-readable storage media, executable by the computer system to cause the computer system to display, on the display system, a number of highest ranked combined results in the combined results with the aggregate scores for the number of highest ranked combined results in the ranked order.

26. The computer program product of claim 24, the program code, stored on the computer-readable storage media, executable by the computer system to cause the computer system to display, on the display system, the combined results in the ranked order with the aggregate scores and a graphical display of individual scores for the search terms associated with the document in each combined result in the combined results comprises:

program code, stored on the computer-readable storage media, executable by the computer system to cause the computer system to identify a score for each search term contributing to an aggregate score in each combined result in the combined results;

program code, stored on the computer-readable storage media, executable by the computer system to cause the computer system to select a graphical indicator for each score identified for each search term contributing to the aggregate score in each combined result in the combined results to form graphical indicators that indicate how often the search term is present in the document relative to other search terms in the document, wherein the graphical indicator comprises one of a color, an icon, a pictogram, an ideogram, an image, text, animation, bolding, a line, or an arrow;

program code, stored on the computer-readable storage media, executable by the computer system to cause the computer system to display the documents in a ranked order based on the combined results; and program code, stored on the computer-readable storage media, executable by the computer system to cause the computer system to display the graphical indicators for each of the documents in graphical association with the documents.

27. The computer program product of claim 26, wherein the program code, stored on the computer-readable storage media, executable by the computer system to cause the computer system to display the graphical indicators for each of the documents in a graphical association with the documents comprises:

program code, stored on the computer-readable storage media, executable by the computer system to cause the computer system to display the graphical indicators for each of the documents in the graphical association with the documents as a heat map.

28. The computer program product of claim 24, wherein the scores are term frequency-inverse document frequency (tf-idf) scores.

29. The computer program product of claim 24 further comprising:

seventh program code, stored on the computer-readable storage media, executable by the computer system to cause the computer system to identify a set of key concepts in a selected document;

eighth program code, stored on the computer-readable storage media, executable by the computer system to cause the computer system to determine features for the key concepts in the selected document in which the document, the key concepts, and the features form a training dataset; and ninth program code, stored on the computer-readable storage media, executable by the computer system to cause the computer system to train a machine learning model using the training dataset, wherein the machine learning model is trained to determine an importance of candidate search terms from an input document recommend a set of the candidate search terms.

30. The computer program product of claim 29 further comprising:

tenth program code, stored on the computer-readable storage media, executable by the computer system to cause the computer system to add negative samples to the training dataset in which the negative samples include terms that are not key terms.

31. The computer program product of claim 29 further comprising:

tenth program code, stored on the computer-readable storage media, executable by the computer system to cause the computer system to generate, by the machine learning model, the candidate search terms in response to receiving the selected document; and eleventh program code, stored on the computer-readable storage media, executable by the computer system to cause the computer system to display the set of the candidate search terms in a graphical user interface on the display system.

32. The computer program product of claim 24 further comprising:

seventh program code, stored on the computer-readable storage media, executable by the computer system to cause the computer system to identify a prior query comprising prior search terms;

eighth program code, stored on the computer-readable storage media, executable by the computer system to cause the computer system to determine cooccurrences of the prior search terms in which the cooccurrences of each prior search term with a number of other prior search terms in the prior query comprises how many times a prior search term was used in prior searches in a search term repository and how many times each of the number of other prior search terms was used in the prior searches with the prior search term in the search term repository;

ninth program code, stored on the computer-readable storage media, executable by the computer system to cause the computer system to store the prior query and the cooccurrences of each prior search term with a number of other prior search terms in the prior query in a training data set; and tenth program code, stored on the computer-readable storage media, executable by the computer system to cause the computer system to train a machine learning model to generate candidate search terms from an input search term.

33. The computer program product of claim 32 further comprising:

eleventh program code, stored on the computer-readable storage media, executable by the computer system to cause the computer system to generate, by the machine learning model, candidate search terms in response to receiving the input search term; and twelfth program code, stored on the computer-readable storage media, executable by the computer system to cause the computer system to display the candidate search terms in a graphical user interface on the display system.

34. The computer program product of claim 24, wherein the second program code comprises:

program code, stored on the computer-readable storage media, executable by the computer system to cause the computer system to perform the search on a collection of documents for each search term in the search terms using a fuzzy searching process.

* * * * *